US012694977B1

(12) United States Patent
Kim et al.

(10) Patent No.: US 12,694,977 B1
(45) Date of Patent: Jul. 28, 2026

(54) USING SOUND TO DETERMINE INTRODUCTION OF CONTAGION(S) WITHIN VEHICLES

(71) Applicant: Zoox, Inc., Foster City, CA (US)

(72) Inventors: Nicholas Nakjoo Kim, San Jose, CA (US); Daniel David Baker, San Francisco, CA (US)

(73) Assignee: Zoox, Inc., Foster City, CA (US)

( * ) Notice: Subject to any disclaimer, the term of this patent is extended or adjusted under 35 U.S.C. 154(b) by 645 days.

(21) Appl. No.: 17/334,038

(22) Filed: May 28, 2021

(51) Int. Cl.
| | |
|---|---|
| *G16H 40/67* | (2018.01) |
| *G06V 20/59* | (2022.01) |
| *G16H 50/20* | (2018.01) |
| *G16H 50/80* | (2018.01) |
| *H04R 3/00* | (2006.01) |

(52) U.S. Cl.
CPC ............. *G16H 40/67* (2018.01); *G06V 20/59* (2022.01); *G16H 50/20* (2018.01); *G16H 50/80* (2018.01); *H04R 3/00* (2013.01)

(58) Field of Classification Search
None
See application file for complete search history.

(56) References Cited

U.S. PATENT DOCUMENTS

| | | | |
|---|---|---|---|
| 2011/0301997 A1* | 12/2011 | Gale ................. | G06Q 10/1097 |
| | | | 705/7.26 |
| 2018/0011975 A1* | 1/2018 | Zhang .................... | G16H 70/00 |
| 2021/0391089 A1* | 12/2021 | Eswara ................. | G06V 20/53 |
| 2021/0402936 A1* | 12/2021 | Mann ........................ | A61L 2/10 |
| 2022/0028556 A1* | 1/2022 | Tiwari ............. | B60W 60/0024 |
| 2022/0176779 A1* | 6/2022 | Ghannam ............ | G06V 10/143 |
| 2022/0254509 A1* | 8/2022 | Sheriff .................... | G16H 40/67 |
| 2022/0277764 A1* | 9/2022 | Ciliberti ................. | G16H 10/60 |
| 2023/0140151 A1* | 5/2023 | Rezai ................... | A61B 5/7264 |
| | | | 600/301 |

* cited by examiner

*Primary Examiner* — Hongye Liang
(74) *Attorney, Agent, or Firm* — Lee & Hayes, P.C.

(57) ABSTRACT

Systems and methods may determine whether contagion(s) are being spread within a vehicle using sound and/or other sensor data. The vehicle may include sensors, such as microphones, cameras, and the like, that continuously or periodically monitor sound and other conditions in an interior of the vehicle and generate sensor data for use in determining whether contagion(s) have been introduced into the vehicle. In the case of sound, audio data generated by the microphones, for example, may represent acoustic characteristic(s) associated with the sound(s) produced by the occupant(s). The introduction of contagion(s) may be used when determining whether to perform action(s) associated with sanitizing the vehicle and/or otherwise reducing a spread of viruses, bacteria, and/or germs among the occupant(s) and/or within the vehicle.

21 Claims, 5 Drawing Sheets

Figure 4:
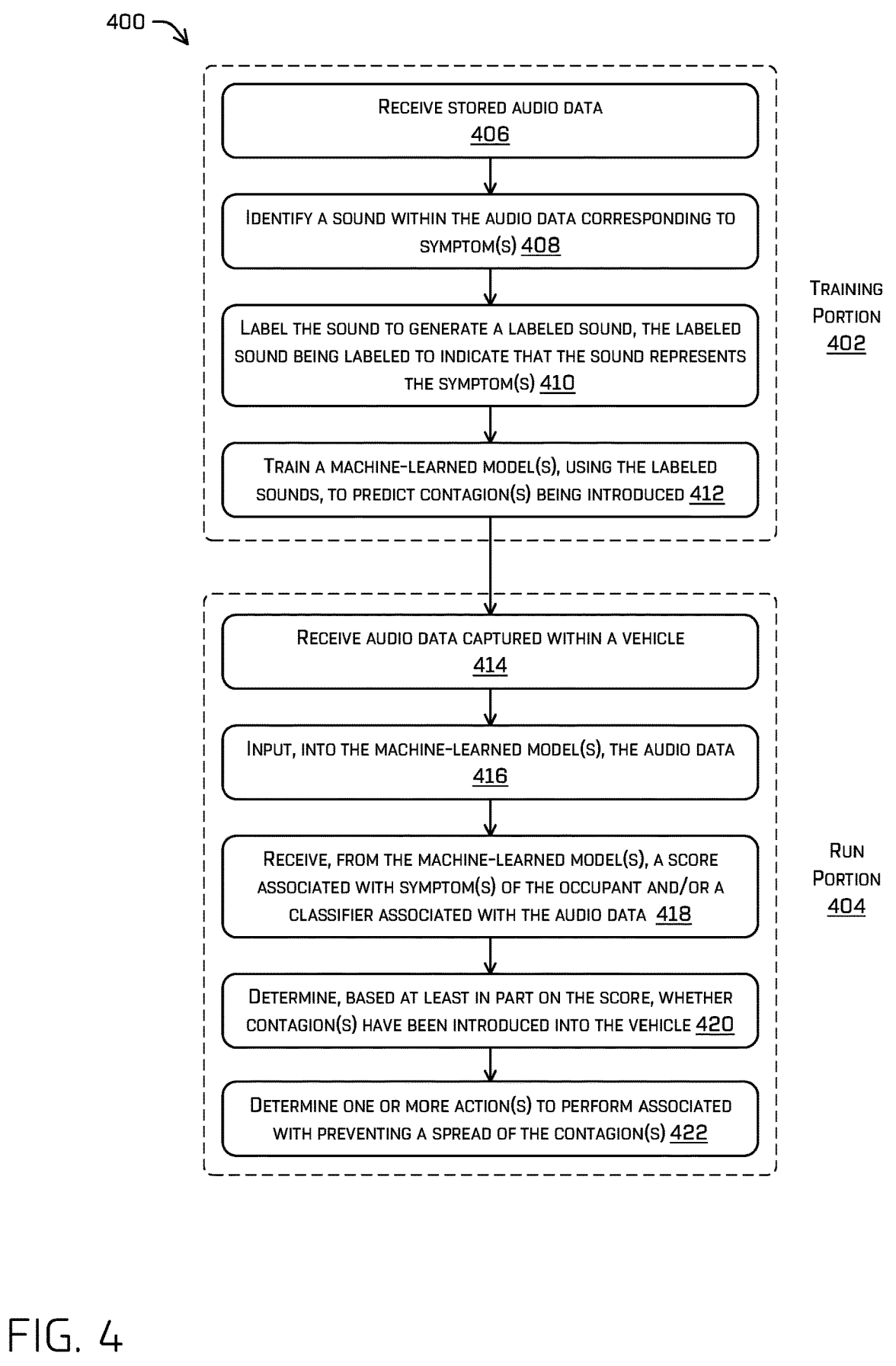

400 ⤸

RECEIVE STORED AUDIO DATA
406

↓

IDENTIFY A SOUND WITHIN THE AUDIO DATA CORRESPONDING TO
SYMPTOM(S) 408

↓

LABEL THE SOUND TO GENERATE A LABELED SOUND, THE LABELED
SOUND BEING LABELED TO INDICATE THAT THE SOUND REPRESENTS
THE SYMPTOM(S) 410

↓

TRAIN A MACHINE-LEARNED MODEL(S), USING THE LABELED
SOUNDS, TO PREDICT CONTAGION(S) BEING INTRODUCED 412

TRAINING
PORTION
402

RECEIVE AUDIO DATA CAPTURED WITHIN A VEHICLE
414

↓

INPUT, INTO THE MACHINE-LEARNED MODEL(S), THE AUDIO DATA
416

↓

RECEIVE, FROM THE MACHINE-LEARNED MODEL(S), A SCORE
ASSOCIATED WITH SYMPTOM(S) OF THE OCCUPANT AND/OR A
CLASSIFIER ASSOCIATED WITH THE AUDIO DATA 418

↓

DETERMINE, BASED AT LEAST IN PART ON THE SCORE, WHETHER
CONTAGION(S) HAVE BEEN INTRODUCED INTO THE VEHICLE 420

↓

DETERMINE ONE OR MORE ACTION(S) TO PERFORM ASSOCIATED
WITH PREVENTING A SPREAD OF THE CONTAGION(S) 422

RUN
PORTION
404

USING SOUND TO DETERMINE INTRODUCTION OF CONTAGION(S) WITHIN VEHICLES

BACKGROUND

Coughs, sneezes, sniffles, and the like are common symptoms of being sick. Additionally, these symptoms may lead to the excretion of body fluids (e.g., air, saliva, mucus, etc.). In enclosed environments, such as vehicles, these symptoms may lead to the spread of viruses, bacteria, and/or other germs. This may lead to increased exposure and/or other occupants of the vehicle becoming sick. In such instances, occupants may feel unsafe and/or ill-protected.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features. The systems depicted in the accompanying figures are not to scale and components within the figures may be depicted not to scale with each other.

FIG. 4 illustrates an example process for training a machine learned model for use in determining whether contagions have been introduced into a vehicle, according to an example of the present disclosure.

DETAILED DESCRIPTION

Figure 1:
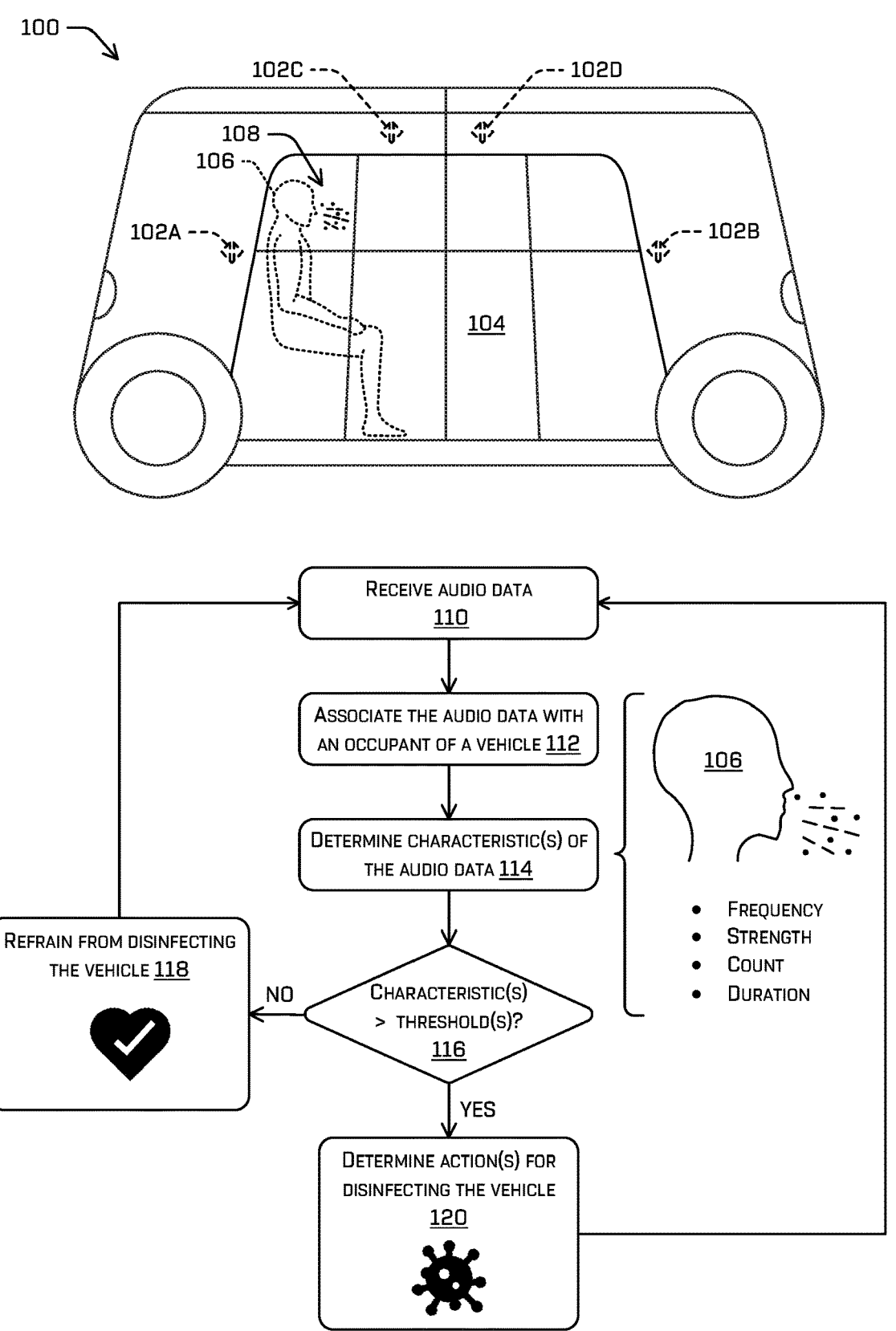
FIG. 1 illustrates an example vehicle including one or more microphones for determining whether a contagion has been introduced into the vehicle, according to an example of the present disclosure.

This application relates to systems and methods that determine whether contagions have been introduced into a vehicle and/or whether the vehicle is in need of disinfecting based on sound and/or other sensor data captured within the vehicle. The vehicle may include one or more sensors, such as microphones, cameras, and the like, that continuously or periodically monitor sound and other conditions in an interior of the vehicle and generate sensor data (e.g., audio data, image data, etc.) for use in determining to sanitize or otherwise disinfect the vehicle. In the case of sound, audio data generated by the microphones, for example, may represent acoustic characteristic(s) associated with the sound(s) produced by the occupant(s). In some instances, an audio signature associated with the sound(s) may be compared against one or more reference audio signatures to determine whether contagions have been introduced into the vehicle. Additionally, or alternatively, machine-learned models may be configured to receive the audio data and/or the audio signatures as an input and output indications associated with whether contagions have been introduced into the vehicle. The presence of contagions may be used when determining whether to perform one or more action(s) associated with sanitizing the vehicle and/or otherwise reducing a spread of viruses, bacteria, and/or germs among the occupant(s) and/or within the vehicle. For example, if the audio data indicates that an occupant is coughing, the vehicle may be sanitized, may be put out of service, and so forth. In some instances, the one or more action(s) associated with sanitizing the vehicle may be performed in instances where one or more thresholds are satisfied. For example, if an occupant coughs more than a threshold number of times within a given period of time, or a strength of the cough(s) is/are greater than a threshold strength, the one or more action(s) may be undertaken. Additionally or alternatively, if the audio data is determined or predicted to be associated with a contagious health condition (e.g., cold, flu, etc.), the one or more action(s) may be undertaken. As such, occupant(s) of the vehicle may be protected from the spread of germs.

In some instances, the microphones may be disposed within the vehicle, such as in a passenger compartment of the vehicle. In some instances, the microphones may be arranged to detect speech of an occupant of the vehicle. In this manner, the microphones that capture speech input of the occupant may also be utilized to generate the audio data utilized to determine whether contagions have been introduced into the vehicle. That is, pre-existing microphones of the vehicle may be used to monitor conditions within the vehicle. The passenger compartment may include any number of microphones for determining a source of the sound (e.g., amongst multiple occupant(s)). For example, the microphones may be disposed on a ceiling, sides, floor of the passenger compartment and/or within components of the passenger compartment (e.g., display, user interface, seats, etc.). Microphones may also be disposed within the occupant devices (e.g., phone).

In some instances, the vehicle may include a monitoring component that monitors sounds produced by the occupant(s). The monitoring component, for example, may receive the audio data and process the audio data for use in classifying the sound and determining whether contagions were introduced into the vehicle. In some instances, the audio data may be processed to remove background noise (e.g., road noise, motor noise, music being played, etc.). In this way, the portion of the audio data attributable to the sound may be isolated and/or the quality of the audio data may be improved to classify sounds within the vehicle.

Additionally, the audio data may be processed to determine or discern a type of sound produced by the occupant(s). For example, the audio data may be processed to be able to discern between user speech and other sounds produced by the occupant(s), such as coughing, sneezing, sniffling, throat clearing, and so forth. As part of this process, the audio data (or more generally, the sounds) may be classified (e.g., speech versus other occupant-produced sounds). Here, in some instances, trained machine-learned model(s) may be used to determine a type of the sound produced by the occupant(s) for use in determining the type of sound is associated with contagions being introduced into the vehicle. In some instances, the audio data may be used to generate audio signatures that are compared against reference audio signatures associated with various sounds. For example, upon capturing audio data associated with the occupant, an audio signature of the audio data may be compared against reference audio signatures to determine whether the audio data is representative of a cough, sneeze, user speech, sniffling, music, and so forth. This may aid in the determination of the type of sound. As such, in some instances, multiple reference audio signatures may be used for comparison with the generated audio signature to determine a type of sound produced by the occupants (e.g., based on their frequency, pitch, amplitude, and so forth). Such audio signature may additionally, or alternatively, be used to filter out background noises (e.g., motor, brakes, etc.).

The audio data, or the audio signatures, may also be processed to extract features or characteristic(s) of the sound. In some instances, the monitoring component may determine, using the machine-learned model(s), characteristic(s) of the sound. In some instances, those sound(s) generated by the occupant(s) other than user speech may be analyzed for the characteristic(s). In some instances, the characteristic(s) of the sound(s) may include a frequency of the sound(s), a strength of the sound(s) (e.g., energy level, decibel level, etc.), a number of times the sound(s) is detected, and/or a duration of the sound(s). Further, in some instances, the machine-learned model(s) may be used to determine a score associated with contagions being introduced (e.g., likelihood) and/or classifiers of the sounds (e.g., coughs, sneezes, etc.). The classifiers may be indicative of contagions being introduced into the vehicle. Moreover, the classifications may be used to indicate cough(s) that are associated with common cold and/or flu viruses or cough(s) that are associated with COVID 19 (e.g., dry cough, wet cough, etc.). Such scores may indicate a severity of the contagion(s) and/or whether the coughs, for example, are of concern.

The classification and/or the characteristic(s) may be used to determine whether the sounds produced by the occupant(s) are indicative of contagions being introduced into the vehicle. These determinations may be compared against respective thresholds for use in determining whether to perform action(s) to increase a cleanliness of the vehicle. For example, if an occupant coughs more than a threshold number of times, if the cough(s) include a strength greater than a threshold strength, if the coughs occur at a frequency greater than a threshold frequency, and/or if the coughs last for longer than a threshold amount of time, the one or more action(s) may be undertaken.

In some instances, the action(s) may include scheduling the vehicle for maintenance (e.g., to replace air filter(s)), sanitizing the vehicle and/or parts of the vehicle (e.g., sanitizing spray, disinfectant wipes, etc.), taking the vehicle out of service, limiting ride-share, lowering windows, adjusting a temperature within the vehicle, circulating the air through a HEPA filter, controlling a HVAC system of the vehicle, circulating outside air within the vehicle, exposing an interior of the vehicle to ultraviolet (UV) light (e.g., UVC-Radiation) or other disinfecting procedures, and so forth. These action(s), when performed, may attempt to eliminate the contagions, isolate the contagions, and/or otherwise reduce the likelihood of spreading the contagion amongst occupant(s) of the vehicle. In some instances, at least some of the action(s) may be performed after the occupant(s) exit the vehicle. Moreover, the type of action performed may be based at least in part on the severity of the contagion being introduced. For example, different actions may be performed depending on the severity at which the contagion has been introduced into the vehicle. If an occupant coughs once, for example, a first action such as controlling the HVAC may be performed. However, if the occupant coughs ten times within a minute, a second action such as scheduling the vehicle for sanitization may be performed. Here, the degree to which the vehicle is sanitized, or the response to contagions being introduced into the vehicle, may be based on the severity of the contagion being introduced and/or the symptoms of the occupant.

The sound(s) may be associated with respective occupant(s) of the vehicle. This may allow the sound(s) to be analyzed for the characteristic(s) when determining whether to perform the action(s). Associating the sound(s) with respective occupant(s) may include comparing signal strengths of the audio data (or signals) generated by the microphones for localizing the sound(s) within the passenger compartment and determining which occupant generated the sound. Additionally, or alternatively, such determination may be based on other sensor data (e.g., cameras, weight sensors in the seat(s), etc.). In this manner, the monitoring component may know which occupant previously produced sound for use in determining the health of the occupants, respectively.

In some instances, if occupants introduced contagions, and action(s) have been performed to sanitize the vehicle, in future instances the occupants may restricted from riding in the vehicle and/or may have to satisfy certain contains. For example, if during a previous trip an occupant coughed and as a result, the vehicle was sanitized, prior to allowing the occupant to ride in the vehicle, the occupant may be prompted to wear a mask. Additionally, or alternatively, the occupant may be asked whether they have seen a doctor, if they have been diagnosed with illnesses, and so forth. Such prompts may limit contagious occupants riding within the vehicle in order to reduce a spread of contagions amongst other occupants. However, the occupant may schedule individual rides for himself or herself, but may be restricted from ride sharing.

Although the above discussion is with regard to using audio data for use in determining whether to sanitize the vehicle, other sensor data may additionally or alternatively be used. For example, sensor data captured by other sensor(s) of the vehicle may additionally, or alternatively, be used when determining to sanitize the vehicle. For example, the vehicle may include cameras that capture image data depicting the occupant. The image data may be analyzed to determine physical characteristics of the occupant, such as perspiration, complexion, eye gaze, etc. The image data may also indicate pupil dilation of the passenger. As an additional example, temperature data associated with a temperature inside the passenger compartment may also be used. Still an infrared (IR) camera may be used to determine a temperature of the passenger. These additional characteristic(s) may further be utilized to determine a health associated with the occupant and/or whether the occupant is at risk of spreading contagions. In these examples, the one or more machine-learned model(s) may be used to analyze the sensor data to predict whether the occupant is contagious or whether contagions have been introduced or are likely to be introduced into the vehicle.

By way of example, and to illustrate, envision that a vehicle is transporting an occupant. During transport, the occupant may produce various sounds such as talking on the phone, using commands to which the vehicle (or components thereof) is responsive, singing, yawning, clapping, coughing, sneezing, and so forth. Additionally, sounds may be generated by component(s) of the vehicle (e.g., radio, brakes, etc.). The sounds may be captured by the microphones and corresponding audio data (or audio signals) may be generated. The audio data may be analyzed to determine a source of the sound (e.g., occupant, vehicle component, road noise, etc.), features of the sound, and/or a type of the sound. For example, the sound may be user speech in which the user requests the vehicle to play certain music. In these instances, the audio data may not be indicative of contagions being introduced into the vehicle. Comparatively, if the user produces sound, such as a cough or sneezing, these types of sounds may be indicative of contagions being introduced. To aid in this decision, as noted above, machine-learned model(s) may accept the audio data as an input and output an indication that classifies the sound (e.g., cough). The sound(s) generated by the users may be tracked and recorded to determine the severity at which contagions have been introduced and/or whether the vehicle is in need of disinfecting. For example, if the occupant coughs once within a five minute period of time, this may not be indicative of contagions being introduced into the vehicle (or a threshold amount of contagions). Alternatively, if the user coughs five times within a one minute period of time, this may be indicative of contagions being introduced, or that contagions are being spread, within the vehicle. Such determination may be used for disinfecting the vehicle or otherwise preventing the spread of the contagion within the vehicle and amongst occupants. However, characteristics of coughs of the occupant, other than frequency, may be used for determining the health of the occupant. Moreover, other sounds of the occupant, such as sneezing or throat clearing, may be used to determine whether contagions have been introduced.

In instances where contagions are introduced the vehicle may be sanitized, for example. This may involve the vehicle releasing cleansing agents within the passenger compartment, whether before, during, or after the occupant exits the vehicle. In some instances, the cleansing agents may be liquid, vapor, gas, or any combination thereof. Examples of such cleansing agents may include, for example, ethanol, isopropyl alcohol, hydrogen peroxide, benzalkonium chloride, ozone, and steam. UV light may also serve to disinfect the vehicle. Further, antimicrobial sprays may be introduced into the vehicle and/or electrostatic sprayers may be used in combination with sprays and/or agents. Additionally, or alternatively, other actions may be performed for reducing the spread of contagions. For example, if contagions have been introduced, the vehicle may not accept ride-share requests, a limited number of occupants may be permitted within the vehicle, and/or the vehicle compartment may be purged with ambient air. Such action(s) may attempt to reduce the spread of contagions amongst the occupant(s) and/or within the vehicle. As such, using the techniques disclose herein, occupant safety may be increased and occupants may feel more comfortable when traveling within the vehicle.

The systems and methods described herein therefore allow for the determination of contagions being introduced for use in disinfecting the vehicle. Such determination may be made in real-time, using microphones of the vehicle, to prevent the spread of germs. For example, sounds generated by the occupant may be monitored for discerning a type of sound produced by the occupant. This allows the sounds to be classified for use in determining whether contagions have been introduced, such as a cough, sneeze, etc. Such systems and methods enable such determination without human interference (e.g., in the case of driverless and/or autonomous vehicles when occupants may not be aware of symptoms of previous occupants). In this way, occupants of the vehicle may trust that the vehicle is sanitized and safe before riding in the vehicle.

Although the above disclosure is described in use for determining occupant health within a vehicle, the systems and methods describe herein may be applicable to other environments and/or modes of transportation (e.g., bus, airplane, boat, etc.). Additionally, although the above discussion is with regard to sanitizing the vehicle upon detection of coughs, for example, the vehicle may be periodically sanitized (e.g., hourly, daily, etc.) and/or sanitized when one or more conditions are met (e.g., number of occupants in the vehicle, number of occupants her hour, an amount of time an occupant has been in the vehicle, etc.).

The present disclosure provides an overall understanding of the principles of the structure, function, device, and system disclosed herein. One or more examples of the present disclosure are illustrated in the accompanying drawings. Those of ordinary skill in the art will understand that the devices and/or the systems specifically described herein and illustrated in the accompanying drawings are non-limiting examples. The features illustrated or described in connection with one example may be combined with the features of other examples. Such modifications and variations are intended to be included within the scope of the appended claims.

FIG. 1 is a schematic view of an example vehicle 100 that includes a plurality of microphones 102A-102D (hereinafter referred to collectively as "the microphones 102" or singularly as "the microphone 102"). In example shown in FIG. 1, the vehicle 100 is a bidirectional, autonomous vehicle that is capable of navigating between locations without human control or intervention. As used herein, a bidirectional vehicle is one that is configured to switch between traveling in a first direction of the vehicle 100 and a second, opposite, direction of the vehicle 100. In other words, there is no fixed "front" or "rear" of the vehicle 100. Rather, whichever longitudinal end of the vehicle 100 is leading at the time becomes the "front" and the trailing longitudinal end becomes the "rear." However, the techniques described herein may be applied to vehicles other than bidirectional vehicles, including autonomous, semi-autonomous, or manually driven vehicles, and robots, and the like.

In some instances, the microphones 102 may be disposed within an interior of the vehicle 100, such as within a passenger compartment 104 in which an occupant 106 resides. The microphones 102 may measure various sounds produced by the occupant 106 (or other occupants) as well as other sounds (e.g., road noise, braking, etc.). In some instances, the microphones 102 may be arranged to capture speech input of the occupant 106 within the vehicle 100, as well as for use in capturing others sounds of the occupant 106 to determine whether the occupant 106 has introduced contagions within the vehicle 100. In the illustrated example, the microphones 102 include a first microphone 102A, a second microphone 102B, a third microphone 102C, and a fourth microphone 102D. The first microphone 102A may be disposed within the passenger compartment 104, proximal to a first longitudinal end of vehicle 100, and a second microphone 102B may be disposed within the passenger compartment 104, proximal to a second longitudinal end of vehicle 100. The third microphone 102C and the fourth microphone 102D may be disposed along a ceiling, within the passenger compartment 104, for example.

However, although illustrated as including four microphones 102, the vehicle 100 may include more than or less than four microphones 102. Additionally, the locations of the microphones 102 on and/or within the vehicle 100 are for illustrative purposes, and it is contemplated that the microphones 102 may be disposed at different locations on the vehicle 100 other than the locations shown in FIG. 1, including in the passenger compartment 104 exterior to the passenger compartment 104. Further, the vehicle 100 may include additional sensors, such as inertial measurement units (IMUs), temperature sensors, image sensors (e.g., cameras), lidar sensors, radar sensors, time-of-flight (TOF)

sensors, sonar sensors, pressure sensors, strain gauges, humidity sensors, geolocation sensors (e.g., GPS sensors), environmental sensors, piezoelectric sensors, accelerometers, air quality sensors, electrical voltage sensors, electrical current sensors, and the like, for permitting operation of the vehicle 100.

Sounds captured by the microphones 102 may be used for a variety of purposes. For example, at least some of the microphones 102 may capture input from the occupant 106 (e.g., verbal commands) to control or otherwise interact with the vehicle 100 (e.g., volume up, adjust temperature, etc.). In some examples, any or all of the microphones 102 may be used to capture such input. Additionally, the microphones 102 may be used to capture audio associated with a health of the occupant 106. In this way, in some examples, existing microphones of the vehicle 100 may be leveraged to monitor occupant health. For example, as shown in FIG. 1, the occupant 106 may produce a sound 108 associated with coughing. Although describe herein as a cough, the sound 108 may be representative of sneezing, throat clearing, sniffling, other symptoms, and so forth in which contagions may be introduced into the vehicle 100. The microphones 102 may capture the sound 108 and generate audio data. As discussed herein, the audio data may be analyzed to classify the sound 108 (e.g., as a cough) and/or to otherwise characterize the sound 108 (e.g., frequency, duration, strength, etc.). Such classification may be indicative of whether contagions have been introduced, a number of occurrences that contagions have been introduced, and/or a severity of contagions being introduced.

Turning to the flow diagram in FIG. 1, an operation 110 includes receiving audio data. For example, as noted above, the microphones 102 may capture the sound 108 and generate corresponding audio data. In some instances, one or more processing techniques may be performed on the audio data to remove background noise and/or sounds other than the sound 108. For example, the audio data may be processed to identify that the sound 108 was produced by the occupant 106 and/or discern the sound 108 from other sounds in the passenger compartment 104. As an example, the processing techniques may be utilized to determine that the sound 108 corresponds to a cough, as compared to speech of the occupant 106. In some instances, and as discussed herein, audio data associated with coughs, sneezes, sniffling, and/or other symptomatic sounds may be used to determine the occupant health, as compared to speech of the occupant 106 and/or other sounds of the occupant 106 (e.g., grunting). In some instances, this may involve comparing the audio data (or an audio signature) with one or more reference audio signatures to determine that the sound 108 (or the audio data) is representative of a cough. Machine-learned techniques are also envisioned.

An operation 112 may include associating the audio data with an occupant of the vehicle. For example, the microphones 102 be used to determine directionality associated with the audio data. By way of example, if the microphones 102 include an array of microphones for capturing the audio data, then the audio data captured by the array of microphones may be used to determine a location or source of generation of the sound 108. If a first microphone of the microphones 102 of the array is closer to the sound 108 than a second microphone of the microphones 102, then first audio data captured by the first microphone may include a stronger audio signal than second audio data captured by the second microphone, and so on. As such, based on the differing signal strengths in the first audio data, the second audio data, third audio data, and so on, a direction and/or location of the sound 108 may be determined. By localizing the sound 108, the audio data may be associated with a particular occupant of the vehicle 100, such as the occupant 106. This allows for the health of individual occupants to be determined and/or associate contagions with certain occupants.

An operation 114 may include determining characteristic(s) of the audio data. For example, the audio data may be analyzed to determine acoustic properties (e.g., features) of the audio data (or of the sound 108 represented within the audio data). In some instances, this may include determining a frequency of the cough(s) (e.g., every second, every ten seconds, etc.), a number of coughs sensed within the audio data (e.g., one, five, ten, etc.), a duration of the cough(s) (e.g., one second, five seconds, etc.), and/or a strength of the cough(s) (e.g., decibel level). Additionally, previous audio data may be utilized to determine these characteristic(s). For example, first audio data may be generated at a first instance in time in response to a first cough of the occupant 106, second audio data may be generated at a second instance in time in response to a second cough of the occupant 106, and so forth. Here, the operation 114 may include, more generally, determining a number of cough(s) associated within the occupant 106, a frequency of those cough(s), a duration of those cough(s), a strength of those cough(s), and so forth. Occupant profiles may be accessed to aid in this determining and to understand previous cough(s) of the occupant 106, for example.

In some instances, additional characteristic(s) of the occupant may be used. For example, a camera within the passenger compartment may capture image(s) of the occupant. Such image(s) may be used to determine a complexion of the occupant, perspiration of the occupant, an eye gaze of the occupant, a temperature of the occupant, and so forth. These additional characteristic(s) may be used when determining characteristic(s) of the sound, classifying the sound, and/or determining a likelihood of the occupant 106 introducing contagions within the vehicle 100. Further, sensor data captured my other sensors (e.g., weight sensor(s), temperature sensor(s), accelerometer(s), etc.) may be used.

An operation 116 may include determining whether the characteristic(s) are greater than threshold(s). In some instances, the threshold(s) may be associated with a threshold number of coughs over a certain period of time, a threshold strength of the cough, a threshold frequency of the coughs, and/or a duration of the coughs. Other thresholds, or criteria, are contemplated. For example, if the occupant 106 coughs more than the threshold number of times, then the characteristic(s) (e.g., the number of coughs) may be greater than the threshold(s). As another example, if the strength of the coughs is greater than the threshold strength(s), then the characteristic(s) (e.g., strengths) may be greater than the threshold(s). In some instances, any number of threshold(s) may be used. Moreover, in some instances, the threshold(s) may be dynamically determined based on the occupant 106 or may be specific to the occupant. For example, if the occupant 106 has allergies, the threshold may be determined to account for such allergies. That is, if the occupant 106 coughs or sneezes, contagions may be introduced, but the occupant 106 may not be contagious, per se, for spreading germs. Such threshold(s) may be determined by accessing an occupant profile associated with the occupant 106 and determining an identity of the occupant (e.g., during a scheduling of a ride).

Based on the comparison of the characteristic(s) to the threshold(s), a health state associated with the occupant 106 may be determined. For example, if the characteristic(s) do not satisfy the threshold(s), an operation 118 may include refraining from disinfecting the vehicle 100. For example, the vehicle 100 may not need to be sanitized, disinfected, and may be sufficiently clean. That is, even though the occupant 106 coughed, the threshold(s) may not be satisfied. In this sense, the vehicle 100 may be determined to be sufficiently clean and no additional cleaning may be needed. Here, in some instances, the occupant 106 may be determined to be healthy and/or a threshold number of instances of the contagion being introduced into the vehicle 100 may not be satisfied. As such, the vehicle 100 may not need to be cleansed or other actions performed to reduce the spread of germs.

Comparatively, if the characteristic(s) satisfy the threshold(s), an operation 120 may include determining action(s) for disinfecting the vehicle 100 or otherwise preventing the spread of contagions within the vehicle 100. That is, in instances where the health of the occupant 106 is concerning, or unhealthy, or whether contagions have been introduced into the vehicle 100, the action(s) may attempt to limit the spread of such contagions amongst occupants. In some instances, the action(s) may include sanitizing the vehicle 100, scheduling the vehicle 100 for maintenance/sanitizing, limiting a number of occupant(s) in the vehicle 100, adjusting vehicle 100 HVAC or other controls, and so forth. In some instances, the action(s) performed may be based at least in part on the degree to which contagion(s) have been spread throughout the vehicle 100. For example, less intrusive action(s), such as purging air within the vehicle 100 may be performed when less than a threshold number of instance of the contagion being introduced occur. More intrusive action(s), such as scheduling the vehicle 100 for sanitization, may be performed when greater than the threshold number of instances occur.

From the operation 118 and/or the operation 120, additional audio data may be received for determining the health of the occupant 106 (or other occupant(s)) for use in determining whether the contagions have been introduced and/or whether the vehicle is in need of sanitization. As explained herein, in some instances, the vehicle 100 may include a monitoring component that utilizes machine-learned model(s) to analyze the audio for use in determining the occupant health. The monitoring component has also compare an audio signature of the audio data with reference audio signatures for use in classifying the sound and/or determining the characteristic(s).

Figure 2:
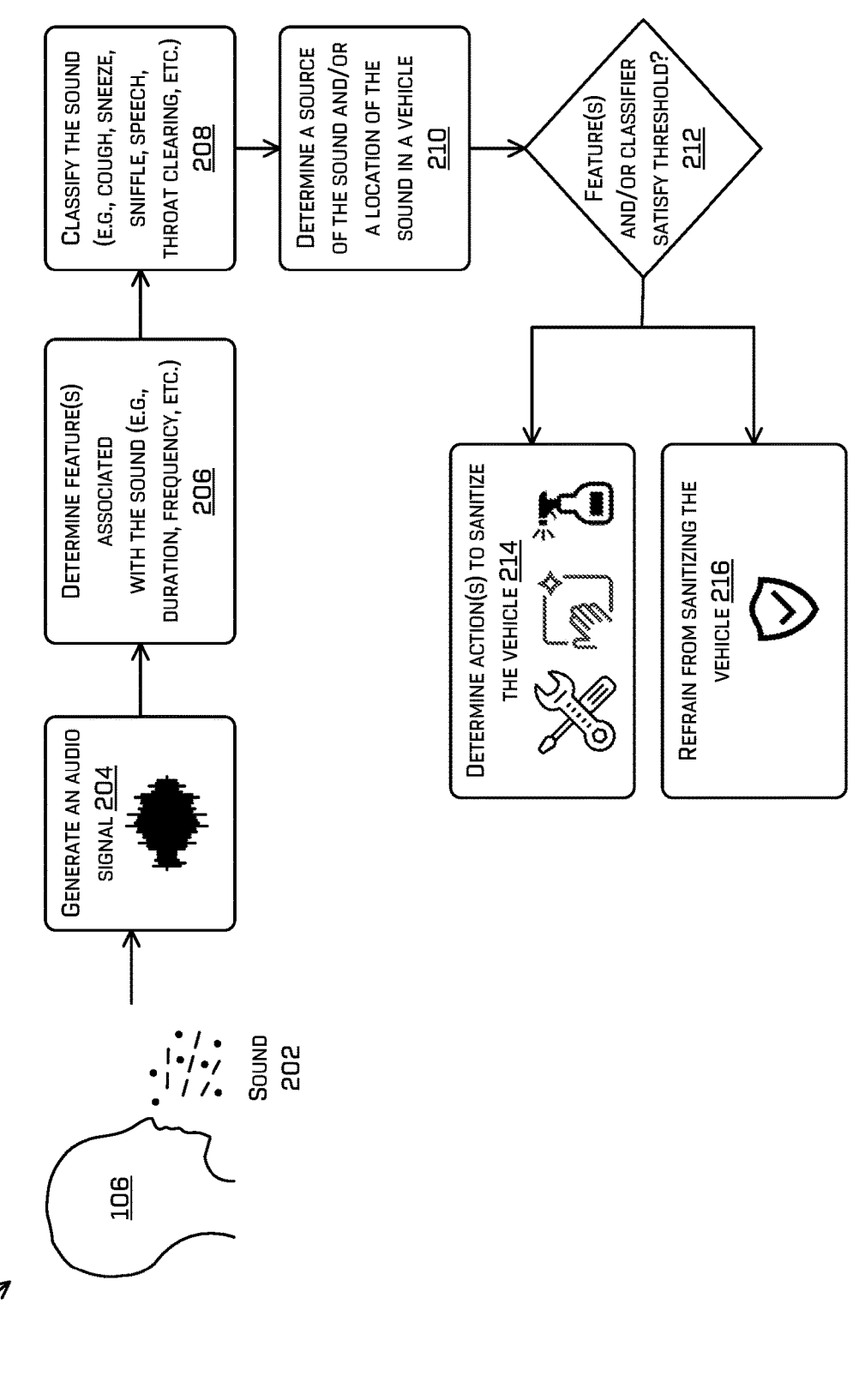
FIG. 2 illustrates an example scenario for characterizing sounds within a vehicle for use in determining whether to disinfect the vehicle, according to an example of the present disclosure.

FIG. 2 illustrates an example scenario 200 associated with processing audio data for use in determining whether to disinfect the vehicle 100. As shown, the occupant 106 may produce a sound 202 (e.g., the sound 108). The sound 202 may be associated with a cough, but the sound 202 may be associated other sounds produced by the occupant 106, such as a sneeze, sniffle, etc. The sound 202 may be captured by the microphones 102, and an audio signal associated with the sound 202 may be generated at 204. In some instances, the audio signal may be generated using signal processing techniques, or the audio signal may be raw, unprocessed audio data.

The scenario 200 may include determining feature(s) associated with the sound at 206. For example, the feature(s) may include a duration of the sound 202, a frequency of the sound 202, a sound pressure level indicative of a strength of an acoustic wave associated with the sound 202, and so forth. In some instances, an average duration, an average frequency, and/or an average sound pressure level of the audio signal may be determined, such as over a certain period of time (e.g., length of cough). Moreover, in the case of sound pressure level a maximum sound pressure level of the audio signal may be determined and/or a minimum sound pressure level of the audio signal may be determined. However, at 206, other feature(s) of the sound 202 may be extracted and in some instances, machine-learned model(s) may be utilized to extract the feature(s).

The scenario 200 may include classifying the sound at 208, for example, based at least in part on the feature(s). In some instances, classifying the sound 202 may include determining whether the sound 202 corresponds to a cough, sneeze, sniffle, speech, throat clearing, other symptoms, and so forth. Classifying the sound may also be indicative of whether the sound 202 is associated with contagions being introduced into the vehicle 100. In some instances, the feature(s) may be compared against feature(s) associated with coughs, sneezes, sniffles, speech, and throat clearing, respectively. For example, a cough may be associated with a first sound pressure level and/or first decibel, a sneeze may be associated with a second sound pressure level and/or second decibel, and so forth. As such, by comparing the feature(s) of the sound 202 to those associated with a cough, sneeze, sniffle, speech, throat clearing, and so forth, the sound 202 may be classified.

Although the above discussion is with regard to comparing the feature(s) to classify the sound 202, other techniques may be used. For example, audio signatures that indicate acoustic properties of a cough, sneeze, sniffle, speech, throat clearing, and so forth may be compared against an audio signature associated with the sound 202 (e.g., pitch, amplitude, frequency, etc.). Such comparison may indicate whether the sound 202 is associated with a cough, sneeze, sniffle, speech, throat clearing, etc.

The scenario 200 may include determining a source of the sound and/or a location of the sound in a vehicle at 210. For example, audio data captured by the array of microphones may be used to determine a location or source of generation of the sound 202 (e.g., time of flight, energy levels, etc.). In some instances, determining the source of the sound 202 may include determining an occupant (e.g., the occupant 106) that produced the sound 202 and associating the sound 202 with the occupant. Additionally, or alternatively, determining the location of the sound 202 may include associating the sound 202 with a particular portion of the vehicle 100 (e.g., front, back, quadrant, etc.) and/or a particular seat of the vehicle 100. In some instances, sensor data generated by other sensor(s) may be used to determine the location and/or source of the sound 202. For example, camera(s) within the vehicle 100 may indicate a location of occupant(s) in the vehicle 100 and/or weight sensor(s) within seats of the vehicle 100 may indicate which seats are being occupied.

The scenario 200 may include determining whether the feature(s) and/or the classifier satisfy a threshold at 212. For example, based on the audio data and/or audio signals captured by the microphones, it may be determined how many times the occupant 106 coughed, sneezed, sniffled, and so forth. Moreover, this determination may also be made for other occupants in the vehicle 100. As such, for each occupant, the number of coughs, sniffles, and so forth may be determined. Previously captured audio data stored in occupant profiles may provide such indications. Additionally, based on the classification of the sound 202, it may be determined whether the sound 202 is indicative of contagions being introduced into the vehicle 100. As such, the feature(s) and/or the classifier of the sound 202 may be used in determining whether the vehicle 100 needs to be sanitized or otherwise disinfected for reducing or eliminating a spread of the contagion.

That is, based on the feature(s) and/or the classifier, the scenario 200 may include determining action(s) to sanitize the vehicle at 214, or may refrain from sanitizing the vehicle at 216. By way of example, in instances where the number of occurrence(s) is greater than a threshold number, the scenario 200 may include determining to sanitize the vehicle 100, perform maintenance on the vehicle 100, and so forth at 214 to reduce the spread of germs. In such instances, the scenario 200 may include determining that the occupant 106 is spreading a contagion within the vehicle 100. Alternatively, if the number of occurrence(s) is not greater than the threshold number, the scenario may include determinizing that the vehicle 100 does not need to be sanitized. In such instances, the scenario 200 may include determining that contagions have not been introduced into the vehicle 100 and/or that less than a threshold number of instances have occurred where contagions are introduced.

Figure 3:
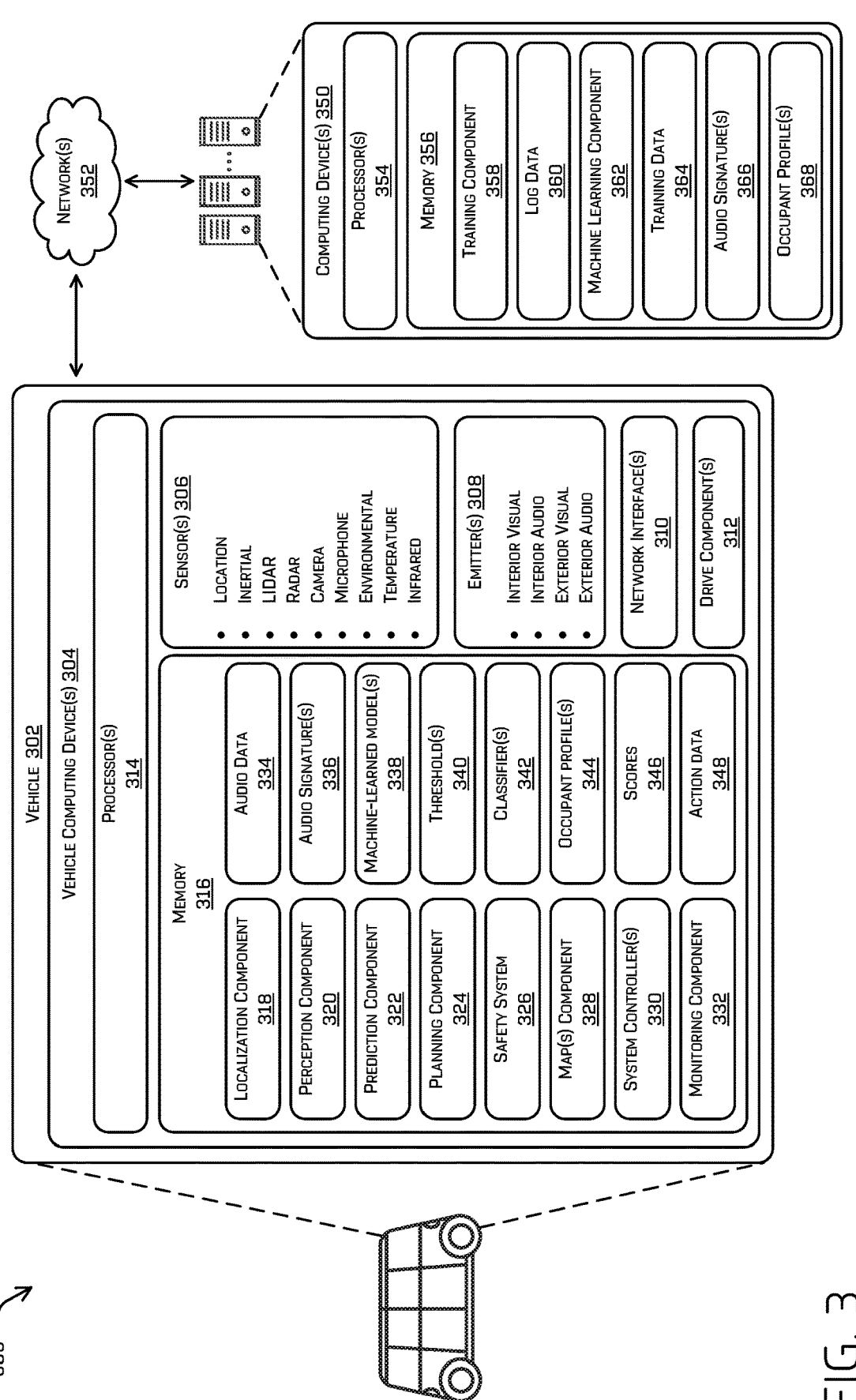
FIG. 3 illustrates a block diagram of an example system for implementing the techniques described herein, according to an example of the present disclosure.

FIG. 3 depicts a block diagram of an example architecture 300 for implementing the techniques discussed herein. In some instances, the example architecture 300 may include a vehicle 302, which may represent the vehicle 100 in FIG. 1. In some instances, the vehicle 302 may be an autonomous vehicle configured to operate according to a Level 5 classification issued by the U.S. National Highway Traffic Safety Administration, which describes a vehicle capable of performing all safety-critical functions for the entire trip, with the driver (or occupant) not being expected to control the vehicle at any time. However, in other examples, the vehicle 302 may be a fully or partially autonomous vehicle having any other level or classification. Moreover, in some instances, the techniques described herein may be usable by non-autonomous vehicles as well.

The vehicle 302 may include one or more vehicle computing device(s) 304, one or more sensor(s) 306, one or more emitter(s) 308, one or more network interface(s) 310 (also referred to as communication devices and/or modems), and/or one or more drive component(s) 312. In some instances, the one or more sensor(s) 306 may include time-of-flight sensors, location sensors (e.g., GPS, compass, etc.), inertial sensors (e.g., inertial measurement units (IMUs), accelerometers, magnetometers, gyroscopes, etc.), lidar sensors, radar sensors, sonar sensors, infrared sensors, cameras (e.g., RGB, IR, intensity, depth, etc.), microphone sensors, environmental sensors (e.g., temperature sensors, humidity sensors, light sensors, pressure sensors, etc.), ultrasonic transducers, wheel encoders, etc. The one or more sensor(s) 306 may include multiple instances of each of these or other types of sensors. For instance, the time-of-flight sensors may include individual time-of-flight sensors located at the corners, front, back, sides, and/or top of the vehicle 302. As another example, the camera sensors may include multiple cameras disposed at various locations about the exterior and/or interior of the vehicle 302. Similarly, the microphone sensors may include multiple microphones disposed at various locations about the exterior and/or interior of the vehicle 302. The one or more sensor(s) 306 may provide input to the vehicle computing device(s) 304.

The one or more emitter(s) 308 may emit light and/or sound. The one or more emitter(s) 308 in this example may include interior audio and visual emitters to communicate with passengers of the vehicle 302. By way of example and not limitation, interior emitters may include speakers, lights, signs, display screens, touch screens, haptic emitters (e.g., vibration and/or force feedback), mechanical actuators (e.g., seatbelt tensioners, seat positioners, headrest positioners, etc.), and the like. The one or more emitter(s) 308 in this example may also include exterior emitters. By way of example and not limitation, the exterior emitters may include lights to signal a direction of travel or other indicator of vehicle action (e.g., indicator lights, signs, light arrays, etc.), and one or more audio emitters (e.g., speakers, speaker arrays, horns, etc.) to audibly communicate with pedestrians or other nearby vehicles, one or more of which may comprise acoustic beam steering technology.

The vehicle 302 may also include one or more network interface(s) 310 that enable communication between the vehicle 302 and one or more other local or remote computing device(s) (e.g., a remote teleoperation computing device) or remote services. For instance, the one or more network interface(s) 310 may facilitate communication with other local computing device(s) on the vehicle 302. Also, the one or more network interface(s) 310 may allow the vehicle 302 to communicate with other nearby computing device(s) (e.g., other nearby vehicles, traffic signals, etc.). The one or more network interface(s) 310 may include physical and/or logical interfaces for connecting the vehicle computing device(s) 304 to another computing device or one or more external networks (e.g., the Internet). For example, the one or more network interface(s) 310 may enable Wi-Fi-based communication such as via frequencies defined by the IEEE 802.11 standards, short range wireless frequencies such as Bluetooth, cellular communication (e.g., 2G, 3G, 4G, 4G LTE, 5G, etc.), satellite communication, dedicated short range communications (DSRC), or any suitable wired or wireless communications protocol that enables the respective computing device to interface with the other computing device(s).

In at least one example, the vehicle 302 may include one or more drive component(s) 312. In some examples, the vehicle 302 may have a single drive component 312. In at least one example, the vehicle 302 may have multiple drive components 312, where individual drive component(s) 312 may be positioned on opposite ends of the vehicle 302 (e.g., the front and the rear, etc.). In at least one example, the drive component(s) 312 may include the one or more sensor(s) 306 to detect conditions of the drive component(s) 312 and/or the surroundings of the vehicle 302. By way of example and not limitation, the sensor(s) 306 may include one or more wheel encoders (e.g., rotary encoders) to sense rotation of the wheels of the drive systems, inertial sensors (e.g., inertial measurement units, accelerometers, gyroscopes, magnetometers, etc.) to measure orientation and acceleration of the drive system, cameras or other image sensors, ultrasonic sensors to acoustically detect objects in the surroundings of the drive system, lidar sensors, radar sensors, etc. Some sensors, such as the wheel encoders may be unique to the drive component(s) 312. In some cases, the sensor(s) 306 on the drive component(s) 312 may overlap or supplement corresponding systems of the vehicle 302 (e.g., sensor(s) 306).

The drive component(s) 312 may include many vehicle systems, including a high voltage battery, a motor to propel the vehicle 302, an inverter to convert direct current from the battery into alternating current for use by other vehicle systems, a steering system including a steering motor and steering rack (which may be electric), a braking system including hydraulic or electric actuators, a suspension system including hydraulic and/or pneumatic components, a stability control system for distributing brake forces to mitigate loss of traction and maintain control, a HVAC system, lighting (e.g., lighting such as head/tail lights to illuminate an exterior surrounding of the vehicle), and one or more other systems (e.g., cooling system, safety systems, onboard charging system, other electrical components such as a DC/DC converter, a high voltage junction, a high voltage cable, charging system, charge port, etc.).

Additionally, the drive component(s) 312 may include a drive manager component. In some instances, the drive manager component may receive and preprocess data from the sensor(s) 306 and to control operation of the various system(s) and/or component(s) of the vehicle 302. In some examples, the drive manager component may include one or more processor(s) and memory communicatively coupled with the one or more processor(s). The memory may store one or more components to perform various functionalities of the drive component(s) 312. Furthermore, the drive component(s) 312 also include one or more communication connection(s) that enable communication by the respective drive system with one or more other local or remote computing device(s).

As shown, the vehicle computing device(s) 304 may include one or more processor(s) 314 and memory 316 communicatively coupled with the one or more processor(s) 314. In the illustrated example, the memory 316 of the vehicle computing device(s) 304 stores a localization component 318, a perception component 320, a prediction component 322, a planning component 324, a safety system 326, a map(s) component 328, one or more system controller(s) 330, and/or a monitoring component 332. Though depicted as residing in the memory 316 for illustrative purposes, it is contemplated that the localization component 318, the perception component 320, the prediction component 322, the planning component 324, the safety system 326, the map(s) component 328, the one or more system controller(s) 330, and/or the monitoring component 332 be accessible to the vehicle computing device(s) 304 (e.g., stored in a different component of vehicle 302) and/or be accessible to the vehicle 302 (e.g., stored remotely).

In the memory 316 of the vehicle computing device(s) 304, the localization component 318 may include functionality to receive data from the sensor(s) 306 to determine a position of the vehicle 302. For example, the localization component 318 may include and/or request/receive a three-dimensional map of an environment and may continuously determine a location of the vehicle 302 within the map. In some instances, the localization component 318 may use SLAM (simultaneous localization and mapping) or CLAMS (calibration, localization and mapping, simultaneously) to receive time-of-flight data, image data, lidar data, radar data, sonar data, IMU data, GPS data, wheel encoder data, or any combination thereof, and the like to accurately determine a location of the vehicle 302. In some instances, the localization component 318 may provide data to various components of the vehicle 302 to determine an initial position of vehicle 302 for generating a trajectory, as discussed herein.

The perception component 320 may include functionality to perform object detection, segmentation, and/or classification. In some examples, the perception component 320 may provide processed sensor data that indicates a presence of an entity that is proximate to the vehicle 302 and/or a classification of the entity as an entity type (e.g., car, pedestrian, cyclist, building, tree, road surface, curb, sidewalk, unknown, etc.). In some instances, the perception component 320 may include functionality to store perception data generated by the perception component 320. In some instances, the perception component 320 may determine a track corresponding to an object that has been classified as an object type. The stored perception data may, in some examples, include fused perception data captured by the vehicle 302. Fused perception data may include a fusion or other combination of sensor data from the sensor(s) 306, such as image sensors, lidar sensors, radar sensors, time of flight sensors, sonar sensors, global positioning system sensors, internal sensors, and/or any combination of these. The stored perception data may additionally or alternatively include classification data including semantic classifications of objects (e.g., pedestrians, vehicles, buildings, road surfaces, etc.) represented in the sensor data.

The stored perception data may additionally or alternatively include track data (positions, orientations, sensor features, etc.) corresponding to motion of objects classified as dynamic objects through the environment. The track data may include multiple tracks of multiple different objects over time. This track data may be mined to identify images of certain types of objects (e.g., pedestrians, animals, etc.) at times when the object is stationary (e.g., standing still) or moving (e.g., walking, running, etc.).

In additional and/or alternative examples, the perception component 320 may provide processed sensor data that indicates one or more characteristics associated with a detected entity and/or the environment in which the entity is positioned. In some examples, characteristics associated with an entity may include, but are not limited to, an x-position (global position), a y-position (global position), a z-position (global position), an orientation, an entity type (e.g., a classification), a velocity of the entity, an extent of the entity (size), etc. Characteristics associated with the environment may include, but are not limited to, a presence of another entity in the environment, a state of another entity in the environment, a time of day, a day of a week, a season, a weather condition, an indication of darkness/light, etc.

The perception component 320 may use perception algorithms to determine a perception based bounding box associated with an object in the environment based on sensor data. For example, the perception component 320 may receive image data from the one or more sensor(s) 306 and classify the image data to determine that an object is represented in the image data. Then, using detection algorithms, the perception component 320 may generate a two dimensional bounding box and/or a perception based three dimensional bounding box associated with the object. The perception component 320 may further generate a three dimensional bounding box associated with the object. The three dimensional bounding box may provide additional information such as a location, orientation, pose, and/or size (e.g., size, width, height, etc.) associated with the object.

The prediction component 322 may generate one or more probability maps representing prediction probabilities of possible locations of one or more objects in an environment. For example, the prediction component 322 may generate one or more probability maps for vehicles, pedestrians, animals, and the like within a threshold distance from the vehicle 302. In some instances, the prediction component 322 may measure a track of an object and generate a discretized prediction probability map, a heat map, a probability distribution, a discretized probability distribution, and/or a trajectory for the object based on observed and predicted behavior. In some instances, the one or more probability maps may represent an intent of the one or more objects in the environment.

The planning component 324 may determine a path for the vehicle 302 to follow to traverse through an environment. For example, the planning component 324 may determine various routes and paths and various levels of detail. In some instances, the planning component 324 may determine a route to travel from a first location (e.g., a current location) to a second location (e.g., a target location). For the purpose of this discussion, a route may be a sequence of waypoints for traveling between two locations. As non-limiting examples, waypoints include streets, intersections, global positioning system (GPS) coordinates, etc. Further, the planning component 324 may generate an instruction for guiding the vehicle 302 along at least a portion of the route from the first location to the second location. In at least one example, the planning component 324 may determine how to guide the vehicle 302 from a first waypoint in the sequence of waypoints to a second waypoint in the sequence of waypoints. In some examples, the instruction may be a path, or a portion of a path. In some examples, multiple paths may be substantially simultaneously generated (i.e., within technical tolerances) in accordance with a receding horizon technique. A single path of the multiple paths in a receding data horizon having the highest confidence level may be selected to operate the vehicle.

In other examples, the planning component 324 may alternatively, or additionally, use data from the perception component 320 and/or the prediction component 322 to determine a path for the vehicle 302 to follow to traverse through an environment. For example, the planning component 324 may receive data from the perception component 320 and/or the prediction component 322 regarding objects associated with an environment. Using this data, the planning component 324 may determine a route to travel from a first location (e.g., a current location) to a second location (e.g., a target location) to avoid objects in an environment. In at least some examples, the planning component 324 may determine there is no such collision free path and, in turn, provide a path which brings vehicle 302 to a safe stop avoiding all collisions and/or otherwise mitigating damage.

In examples, the safety system 326 in addition to or in place of the planning component 324 may alternatively, or additionally, use data from the perception component 320, the one or more sensor(s) 306, and/or the localization component 318, to determine whether a path for the vehicle 302 through an environment will require a sudden change in velocity, a hard stop, or if a collision is unavoidable. For example, the safety system 326 may receive data from the perception component 320, the one or more sensor(s) 306, and/or the localization component 318, regarding objects associated with an environment. Using this data, the safety system 326 may determine a required change in velocity of the vehicle, a predicted change in velocity of the vehicle, a collision, or a predicted collision.

In examples, the planning component 324 and/or the safety system 326 may determine an impact location between the vehicle 302 and the object based at least in part on trajectories of the vehicle 302 and/or the object. For example, planning component 324 and/or safety system 326 may determine that the intersection between the vehicle 302 and the object is on a side, front, rear, etc. of the vehicle 302. In some instances, the planning component 324 and/or the safety system 326 may determine whether the vehicle 302 includes rearward facing occupant(s) and/or forward facing occupant(s) within the vehicle 302, using the trajectory of the vehicle 302 and/or the sensor(s) 306.

In some instances, the planning component 324 and/or safety system 326 may be configured to determine a time associated with change in velocity of the vehicle 302, a predicted change in velocity of the vehicle 302, a collision, or a predicted collision, or whether the change in velocity of the vehicle 302, a predicted change in velocity of the vehicle 302, a collision, or a predicted collision is imminent. The time may be a particular time, such as, for example, 120 milliseconds after 3:05 pm, or it may be a time interval from a time in which change in velocity of the vehicle 302, a predicted change in velocity of the vehicle 302, a collision, or a predicted collision was determined. The time may be determined based on a measured closure rate of the object toward the vehicle 302, a velocity of the vehicle 302, an acceleration of the vehicle 302, a velocity of the object, an acceleration of the object, road conditions, weather conditions, and/or other factors that may affect a closure rate of the object toward the vehicle 302, or vice versa.

The memory 316 may further include one or more map(s) component 328 that may be used by the vehicle 302 to navigate within the environment. For the purpose of this discussion, a map may be any number of data structures modeled in two dimensions, three dimensions, or N-dimensions that are capable of providing information about an environment, such as, but not limited to, topologies (such as intersections), streets, mountain ranges, roads, terrain, and the environment in general. In some instances, a map may include, but is not limited to: covariance data (e.g., represented in a multi-resolution voxel space), texture information (e.g., color information (e.g., RGB color information, Lab color information, HSV/HSL color information), and the like), intensity information (e.g., LIDAR information, RADAR information, and the like); spatial information (e.g., image data projected onto a mesh, individual "surfels" (e.g., polygons associated with individual color and/or intensity)), reflectivity information (e.g., specularity information, retroreflectivity information, BRDF information, BSSRDF information, and the like). In one example, a map may include a three-dimensional mesh of the environment. In some instances, the map may be stored in a tiled format, such that individual tiles of the map represent a discrete portion of an environment, and may be loaded into working memory as needed, as discussed herein. In at least one example, the one or more map(s) component 328 may include at least one map (e.g., images and/or a mesh). In some examples, the vehicle 302 may be controlled based at least in part on the map(s) component 328. That is, the map(s) component 328 may be used in connection with the localization component 318, the perception component 320 (and sub-components), the prediction component 322, and/or the planning component 324 to determine a location of the vehicle 302, identify objects in an environment, generate prediction probability(ies) associated with objects and/or the vehicle 302, and/or generate routes and/or trajectories to navigate within an environment.

In at least one example, the vehicle computing device(s) 304 may include one or more system controller(s) 330, which may be configured to control steering, propulsion, braking, safety, emitters, communication, and other systems of the vehicle 302. These system controller(s) 330 may communicate with and/or control corresponding systems of the drive component(s) 312 and/or other components of the vehicle 302, which may be configured to operate in accordance with a path provided from the planning component 324.

The monitoring component 332 is configured to monitor occupants within the vehicle 302, a health of the occupants within the vehicle 302, whether contagions have been introduced into the vehicle 302, and/or a cleanliness of the vehicle 302 for determining action(s) associated with preventing the spread of germs and/or disinfecting the vehicle 302. More generally, the monitoring component 332 may determine whether the vehicle 302 is sanitized for occupant(s) or whether the vehicle needs to be serviced, cleaned, etc. To aid in this determination, the monitoring component 332 may have access to audio data 334, audio signature(s) 336, machine-learned model(s) 338, and/or threshold(s) 340. Although shown as residing in the memory 316, the audio data 334, the audio signature(s) 336, the machine-learned model(s) 338, and/or the threshold(s) 340 may be accessible to the vehicle computing device(s) 304 (e.g., stored in a different component of vehicle 302) and/or be accessible to the vehicle 302 (e.g., stored remotely).

The audio data 334 is representative of sound(s) captured within the vehicle 302. The audio data 334 may be generated by a plurality of microphones within the vehicle. Sounds captured by the microphones (the audio data 334) may represent sounds produced by occupant(s) (e.g., speech, cough, sneeze, signing, yawning, clapping, etc.), background noise (e.g., wind, road noise, etc.), vehicle noise (e.g., brakes, motor, etc.), and the like. As such, the microphones may be arranged to capture various audio data associated with the occupant(s), the environment, and/or the vehicle 302.

In some instances, the audio data 334 may include raw sensor data (e.g., the audio data 334 that is captured by a microphone of the vehicle 302) and/or processed audio data (e.g., audio data that is processed by a filtering component after being captured by a microphone). For example, a filtering component may filter and/or process the audio data 334 captured by the sensor(s) 306 to remove background noise. In some instances, the filtering component may identify the background noise of the audio data 334 with respect to the audio signature of the sound and remove at least some of the background noise from the audio data 334.

In some instances, the monitoring component 332 receives the audio data 334 from the sensor(s) 306, and uses the audio data 334 to determine the audio signature(s) 336. In some instances, the audio signature(s) 336 may be representative of acoustic properties of the sounds captured within the vehicle 302 (e.g., wavelength, pitch, frequency, amplitude, etc.). The audio signature(s) 336 may additionally, or alternatively, be associated with various pre-determined sound(s), such as speech, coughing, sneezing, and so forth. As an example, an audio signature may be stored that indicates acoustic properties of a sneeze. The audio signature(s) 336 may additionally or alternatively be associated with certain features of sounds, such as sound pressure levels, duration, frequency, and so forth. The audio signature(s) 336 may be utilized for comparison within an audio signature associated with the captured audio data 334 to determine whether the sound is indicative of a sneeze, for example, based on a comparison of the feature(s).

The monitoring component 332 may be configured to determine whether contagions have been introduced into the vehicle 302 based on the comparison of the audio signatures 336. In other words, the monitoring component 332 may receive the audio data 334 captured by microphone(s) of the sensor(s) 306 and determine whether the occupant released contagions by comparing the audio signature 336 to reference audio signature(s). Whether contagions have been introduced may be based on a determination of whether the occupant is coughing, sneezing, and so forth. In some instances, the monitoring component 332 may make this determination based on a single audio data recording or multiple audio data recordings. Rather than determining the introduction of contagion(s) t, the monitoring component 332 may determine whether the vehicle is in need of sanitization based on the sound(s) produced by the occupant and the potential release (or severity) of contagion(s) being introduced into the vehicle 302.

The monitoring component 332 may be configured to determine classifier(s) 342 of the sound, or the audio data 334. For example, based on analyzing the audio data 334 or the audio signature(s) 336, the monitoring component 332 may determine whether the sound corresponds to user speech, a cough, a sneeze, a sniffle, and so forth. Such classifier(s) 342 may be used for further processing of the audio data 334 and for use in determining whether contagion(s) have been introduced. For example, if the sound is classified as user speech, such sound may not be indicative of contagions being introduced (e.g., unrelated to a health of the occupant). Comparatively, if the sound is classified as a cough, this sound may be utilized to determine that contagions were introduced into the vehicle (e.g., related to the health of the occupant). For example, a cough may be indicative of the occupant being sick, unhealthy, symptomatic, contagious, and the like. In some instances, the audio data 334 may be associated with more than one classifier 342 and the monitoring component 332 may determine a most likely classifier 342 (e.g., highest rated).

As part of determining the occupant health, the monitoring component 332 may be configured to compare characteristic(s) of the audio data with threshold(s) 340. In some instances, the characteristic(s) may be stored in association with occupant profile(s) 344. For example, sounds captured in the vehicle 302 may be associated with an occupant (e.g., using time-of-flight techniques, an array of microphones, etc.) and stored in the occupant profile(s) 344. By associating the sound with the occupant(s), the monitoring component 332 may track and record sound(s) generated by the occupant for comparison against the threshold(s) 340.

In some instances, the threshold(s) 340 may correspond to number coughs (or sneezes, sniffles, etc.), a frequency of coughs over a certain period of time, a strength of the coughs, and/or a duration of the coughs. If the occupant coughs the threshold number of times, the characteristic(s) may be determined to satisfy the threshold(s) 340. Additionally, or alternatively, if the occupant coughs longer than the threshold duration, the characteristic(s) may be determined to satisfy the threshold(s) 340. Alternatively, if the occupant only coughs once over a certain period of time, the characteristic(s) may be determined to not satisfy the threshold(s). In some instances, the threshold(s) 340 may be determined to be acceptable level(s) to prevent the spread of germs. In some instances, any number of the characteristic(s) may be compared against respective thresholds for use in determining whether the characteristic(s) satisfy the threshold(s) 340. Moreover, as part of this process, by associating the sound and/or the audio data 334 with the occupant profile(s) 344, previous coughs (or sneezes, sniffles, etc.) of the occupant may be determined. This allows the monitoring component 332 to determine whether the threshold(s) are satisfied.

In some instances, the threshold(s) 340 may be specific to the occupant(s) in the vehicle 302 and may be determined by accessing the occupant profile(s) 344. For example, the occupant profile(s) 344 may indicate that an occupant has allergies, and in instances where the occupant sneezes for example, such occurrence may not satisfy a threshold associated with the occupant being sick or contagious. That is, the sneeze may be associated with the occupant's allergies, as compared to a sickness.

As part of determining the health of the occupant, classifying the sound, and/or determining the characteristic(s), the monitoring component 332 may have access to machine-learned model(s) 338. In some instances, the monitoring component 332 may utilize one or more machine-learned model(s) 338 for determining the health of the occupant and/or whether contagion(s) have been introduced into the vehicle 302. The machine-learned model(s) 338 may analyze the audio data 334, or other information, for use in making such determinations, classifying the sound, and/or determining the characteristic(s) of the sound. In some instances, the machine-learned model(s) 338 may determine or generate scores 346 for the sounds captured by the microphone(s). In some instances, individual scores 346 may be determined by accessing audio data 334 associated with an individual sounds captured by the microphones, providing the audio data as input to the machine-learned model(s) 338, and generating, as output from the machine-learned model(s) 338, the score 346 that is associated with the sounds. The scores 346 may be representative of the health of the occupant, the contagiousness of the occupant, the introduced of contagions within the vehicle 302, and so forth. More generally, the score 346 may indicate whether the sound is associated with a symptom of a sickness or whether contagion(s) were introduced. In other words, the scores 346 may be machine-learned scores based on training data (e.g., labels) that indicate which sounds are indicative of coughs, sneezes, and so forth.

In instances where the monitoring component 332 determines that the sounds are indicative of coughs, sneezes, and/or other symptoms, the monitoring component 332 may determine action(s) to perform to disinfect the vehicle 302 and/or increase the safety of occupants within the vehicle 302. In some instances, the action(s) may be stored as action data 348 within the memory 316. Moreover, the action(s) may be performed based on the classifier 342 of the sound, the characteristic(s) of the sound, and/or whether the threshold(s) 340 are satisfied. By way of example and not limitation, the action(s) may include sanitizing the vehicle 302, providing notification(s), disabling the vehicle 302 from accepting new occupant(s), rolling down the window(s), circulating interior air through a HEPA filter, adjusting a temperature within the vehicle, controlling an HVAC of the vehicle 302, exposing an interior of the vehicle 302 to UV light, stopping the vehicle and allowing other occupant(s) to exit the vehicle 302, and so forth. In some instances, at least some of the action(s) may be performed after the occupant(s) exit the vehicle 302. In some instances, the action(s) that are performed may be based on the likelihood of contagion(s) being introduced into the vehicle, the number of occurrence(s) contagion(s) have been introduced, and so forth. For example, the amount of sanitization required to disinfect the vehicle 302 may be based on the severity of contagion(s) being introduced into the vehicle 302.

In some instances, other of the memory-stored components discussed herein may include any models, algorithms, and/or machine learning algorithms. For example, in some instances, components in the memory 316 such as the localization component 318, the perception component 320, the prediction component 322, the planning component 324, the monitoring component 332, and the filtering component may be implemented as a neural network.

The vehicle 302 may connect to computing device(s) 350 via a network(s) 352 and may include one or more processor(s) 354 and memory 356 communicatively coupled with the one or more processor(s) 354. In at least one instance, the one or more processor(s) 354 may be similar to the processor(s) 314, and the memory 356 may be similar to the memory 316. The memory 356 may store a training component 358, log data 360, a machine learning component 362, training data 364, one or more audio signatures 366 that are associated with vehicle components, such as components of vehicle 302, and/or the occupant profile(s) 344 (which may be similar to, or include different occupant profiles than the occupant profile(s) 344).

The log data 360 may include historical and/or prerecorded audio data obtained from a computing system of the vehicle 302 (and/or other vehicles, etc.), which captured and stored the audio data. The log data 360 may include raw audio data and/or processed audio data. The training component 358 may generate the training data 364 using the log data 360. For instance, the training component 358 may label audio data associated with sounds captured within the vehicle and/or measure parameters and/or characteristics of the sounds associated with the audio data 334. The audio data 334 and/or the measured parameters or characteristics may be obtained from the log data 360 and/or the audio signatures 366. The label may include an indication of sound (e.g., cough) associated with and/or any other characteristics of the sound (e.g., sound pressure level) at the time the audio data was captured and/or at one or more times subsequent to the time the audio data was captured. The training component 358 may then use the training data 364 to train the machine learning component 362 to predict a health of the occupant, the perceived sound, a cleanliness of the vehicle 302, and/or contagion(s) being spread based at least in part on receiving, as an input, the audio data 334 and/or the audio signatures 366 (or the audio signatures 336).

The memory 356 of the computing device(s) 350 may additionally store the audio signatures 366. In some instances, the audio signatures 366 may include one or more reference audio signatures associated with the sounds (e.g., cough, user speech, etc.). In some instances, the audio signature(s) 366 may be similar to the audio signatures 336. In some examples, the audio signatures 366 may be sent to the vehicle computing device(s) 304 via the network(s) 352. Additionally, the audio signature 366 may be sent to the computing device(s) 350.

The audio data 334 may be sent to the computing device(s) 350 via the network(s) 352 to be used as the log data 360 and/or training data 364. For example, the vehicle 302 may send audio data 334 to one or more computing device(s) 350 via the network(s) 352. In some examples, the vehicle 302 can send raw audio data to the computing device(s) 350. In other examples, the vehicle 302 can send processed audio data and/or representations of the audio data to the computing device(s) 350. In some examples, the vehicle 302 can send audio data to the computing device(s) 350 at a particular frequency, after a lapse of a predetermined period of time, in near real-time, etc. In some cases, the vehicle 302 may send audio data 334 (raw or processed) to the computing device(s) 350 as one or more log files.

In some examples, the occupant profile(s) 368 may indicate a health of the occupants for use in contact tracing, providing notification(s) to the occupant(s), and so forth and may include a log indicating sounds associated with the occupants. Although depicted in FIG. 3 as residing in memory of the computing device(s) 350, in at least some examples and as shown, some of the occupant profile(s) 368 may be stored locally at the vehicle 302. In some examples, the sounds and/or audio data stored in the occupant profile(s) 368 may be used to label the log data 360 for use in training the machine learned model(s) of the machine learning component 362 (e.g., the machine-learned model(s) 338) and/or the monitoring component 332 to predict an operating status of components.

The processor(s) 314 of the vehicle computing device(s) 304 and/or the processor(s) 354 of the computing device(s) 350 may be any suitable processor capable of executing instructions to process data and perform operations as described herein. By way of example and not limitation, the processor(s) 314 and 354 may comprise one or more Central Processing Units (CPUs), Graphics Processing Units (GPUs), or any other device or portion of a device that processes electronic data to transform that electronic data into other electronic data that may be stored in registers and/or memory. In some examples, integrated circuits (e.g., ASICs, etc.), gate arrays (e.g., FPGAs, etc.), and other hardware devices may also be considered processors in so far as they are configured to implement encoded instructions.

The memory 316 of the vehicle computing device(s) 304 and/or the memory 356 of the computing device(s) 350 are examples of non-transitory computer-readable media. The memory 316 and 356 may store an operating system and one or more software applications, instructions, programs, and/or data to implement the methods described herein and the functions attributed to the various systems. In various implementations, the memory 316 and 356 may be implemented using any suitable memory technology, such as static random access memory (SRAM), synchronous dynamic RAM (SDRAM), nonvolatile/Flash-type memory, or any other type of memory capable of storing information. The architectures, systems, and individual elements described herein may include many other logical, programmatic, and physical components, of which those shown in the accompanying figures are merely examples that are related to the discussion herein.

In some instances, aspects of some or all of the components discussed herein may include any models, algorithms, and/or machine learning algorithms. For example, in some instances, the components in the memory 316 and 356 may be implemented as a neural network. As described herein, an exemplary neural network is an algorithm which passes input data through a series of connected layers to produce an output. Each layer in a neural network may also comprise another neural network, or may comprise any number of layers (whether convolutional or not). As may be understood in the context of this disclosure, a neural network may utilize machine learning, which may refer to a broad class of such algorithms in which an output is generated based on learned parameters.

Although discussed in the context of neural networks, any type of machine learning may be used consistent with this disclosure. For example, machine learning or machine learned algorithms may include, but are not limited to, regression algorithms (e.g., ordinary least squares regression (OLSR), linear regression, logistic regression, stepwise regression, multivariate adaptive regression splines (MARS), locally estimated scatterplot smoothing (LOESS)), instance-based algorithms (e.g., ridge regression, least absolute shrinkage and selection operator (LASSO), elastic net, least-angle regression (LARS)), decisions tree algorithms (e.g., classification and regression tree (CART), iterative dichotomiser 3 (ID3), Chi-squared automatic interaction detection (CHAID), decision stump, conditional decision trees), Bayesian algorithms (e.g., naïve Bayes, Gaussian naïve Bayes, multinomial naïve Bayes, average one-dependence estimators (AODE), Bayesian belief network (BNN), Bayesian networks), clustering algorithms (e.g., k-means, k-medians, expectation maximization (EM), hierarchical clustering), association rule learning algorithms (e.g., perceptron, back-propagation, hopfield network, Radial Basis Function Network (RBFN)), deep learning algorithms (e.g., Deep Boltzmann Machine (DBM), Deep Belief Networks (DBN), Convolutional Neural Network (CNN), Stacked Auto-Encoders), Dimensionality Reduction Algorithms (e.g., Principal Component Analysis (PCA), Principal Component Regression (PCR), Partial Least Squares Regression (PLSR), Sammon Mapping, Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA)), Ensemble Algorithms (e.g., Boosting, Bootstrapped Aggregation (Bagging), AdaBoost, Stacked Generalization (blending), Gradient Boosting Machines (GBM), Gradient Boosted Regression Trees (GBRT), Random Forest), SVM (support vector machine), supervised learning, unsupervised learning, semi-supervised learning, etc.

Figure 5:
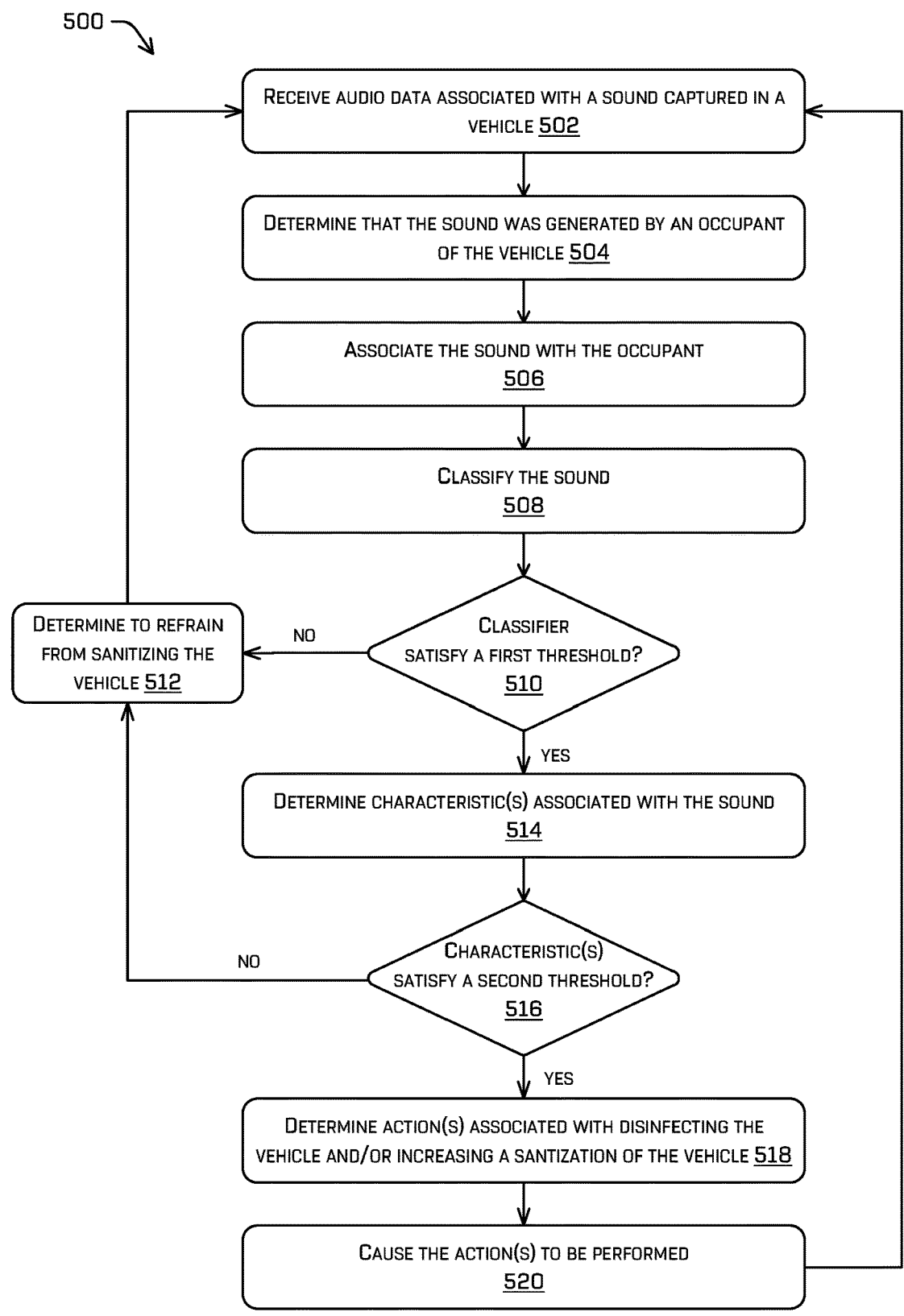
FIG. 5 illustrates an example process for determining whether to disinfect a vehicle, according to an example of the present disclosure.

FIGS. 4 and 5 illustrate various processes related determining sounds captured within a vehicle for use in determining whether to sanitize the vehicle. The processes described herein are illustrated as collections of blocks in logical flow diagrams, which represent a sequence of operations, some or all of which may be implemented in hardware, software, or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-3, although the processes may be implemented in a wide variety of other environments, architectures and systems.

FIG. 4 illustrates an example process 400 associated with training machine-learned model(s), such as the machine-learned model(s) 338, for use in determining a likelihood of spreading contagion(s). The process 400 may be divided into a training portion 402, in which the machine-learned model(s) are trained using training data, and a run portion 404 in which audio data is input into the machine-learned model(s). As discussed herein, in some instances, the machine-learned model(s) 338 may be trained to determine scores related to determining whether sound(s) produced by occupants are indicative of symptom(s), or more generally, a health of the occupant. Moreover, the machine-learned model(s) 338 may be trained to determine whether the sounds are associated with contagion(s) being introduced into the vehicle 302. Although the process 400 describes training machine-learned model(s) to identify symptoms based on sounds within the audio data, it is to be understood that the machine-learned models may be trained to accept other sensor data (e.g., image data).

At 406, the process 400 may include receiving stored audio data. For example, the vehicle computing device(s) 304 and/or the computing device(s) 350 may store and/or maintain a database associated with sounds captured within the vehicle (or the audio data). Regardless of where the audio data is stored, the stored audio data may be organized within a datastore in any suitable manner. In some instances, the stored audio data may include symptom(s), or be stored when the audio data is determined to include sounds that include the symptom(s). Such symptom(s) may be associated with contagion(s) being introduced into the vehicle 302. For example, the audio data may be determined to include symptom(s) by mining the audio data to identify certain types of symptom(s) within the audio data, such as coughs, sneezes, sniffles, allergies, etc. Here, such symptom(s) may be indicative of, or associated with, contagion(s) being excreted into the vehicle 302. In some instances, the stored audio data may be determined to include representations of the symptom(s) based on sound pressure levels, audio signatures, pitch, amplitude, and so forth.

At 408, the process 400 may include identifying a sound within the audio data corresponding to the symptom(s). For example, a portion of the stored audio data corresponding to the symptom(s) may be determined, where the portions of the stored audio data represent potential symptom(s). In some instances, this may include identifying a first portion of the stored audio data corresponding to a first symptom, identifying a second portion of the stored audio data corresponding to a second symptom, and so forth. In some instances, the portion of the stored used as training data may be represented by a set of characteristics that is labeled with a label indicating whether the characteristic is representative of the symptom(s). For example, if a cough has a particular sound pressure level, this "sound pressure level" may be used as one of multiple labels for a particular sound. As an additional example, if a cough has a particular audio signature (e.g., energy levels), this "audio signature" may be used as one of multiple labels for a particular sound. In this manner, a supervised learning approach may be taken to train the machine-learned model(s) to predict sounds that are indicative of coughs. For example, a human labeler may label or indicate portions of sounds that include the symptom(s).

At 410, the process 400 may include labeling (or otherwise associating) ground truth with the sound to generate a labeled sound, the labeled sound being labeled to indicate that the sound represents the symptom(s). Such a label may include one or more measured characteristics of the symptom(s) in the sound. For example, the process 400 may determine a sound pressure level associated with the symptom(s). In some instances, this may include determining a sound pressure level associated with the respective symptoms within the portion(s) of the stored audio data corresponding to the symptom(s). In some instances, based on the sound pressure level, for example, the process 400 may label the symptom to indicate whether the symptom corresponds to a cough, sneeze, sniffle, and so forth. In some instances, the labeled sound(s) may be indicative of a health of the occupant(s). For example, cough(s) may be associated with flu-like or cold-like symptom(s), whereas sniffling may be associated with allergies. In some instances, the number, or occurrence, of the symptom(s) may also be indicative of the health of the occupant.

At 412, the process 400 may include training a machine-learned model, using the labeled sounds, to predict contagion(s) being introduced. In some instances, multiple machine-learned models may be trained to determine instances of the contagion(s) being introduced and/or to classify the symptom as introducing contagion(s), based on the labeled sounds. For example, the stored audio data may represent sound(s) that are associated with coughs. After training the machine-learned model, the machine-learned model may be configured to receive audio data (and/or other sensor data such as image data) for use in detecting sounds, determining symptom(s) present within the sound, and/or whether the sound is indicative of a release of contagion(s) within the vehicle 302.

At 414, the process 400 may include receiving audio data captured within a vehicle. For example, the vehicle may include microphones that generate the audio data. This audio data may be made available to the vehicle computing device(s) 304 and/or the computing device(s) 350. In some examples, the process may additionally or alternatively include other data, such as image data from one or more cameras (e.g., IR camera measured a temperature of the occupant) in the passenger compartment of the vehicle, temperature data from one or more temperature sensors in the passenger compartment of the vehicle, or the like.

At 416, the process 400 may include inputting, into the machine-learned model(s), the audio data. The audio data may be provided as an input to the machine-learned model(s) 338 and the machine-learned model(s) 338 may generate, as an output, one or more scores 346 associated with the sounds.

At 418, the process 400 may include receiving, from the machine-learned model(s), a score associated with symptom(s) of the occupant and/or classifier(s) associated with the audio data. For example, the machine-learned models may score a plurality of sounds within the audio data that are being captured by microphones of the vehicle 302. These scores 346 relate to the probabilities of sounds being indicative of a cough within the vehicle, the sounds not being indicative of a cough within the vehicle, or characteristic(s) of the cough (e.g., duration). For example, in the case of the sound not being representative of a cough a "low" score may relate to a probability of the sound not being associated with a cough. In the case of the sound being indicative of a cough a "high" score may relate to the probability of the sound associated with a cough. Different classifiers, or identifiers, may be used or associated with those sounds that are indicative of a cough and/or not indicative of a cough. Moreover, in those instances where the sounds are not indicative of a cough, the audio data may be input to other trained machine-learned model(s) to determine whether the sounds are indicative of sneezing, sniffling, other symptoms that are utilized to determine a health of the occupant. In some instances, the monitoring component may receive the scores 346 and compare these scores 346 to a threshold, or certain predetermined level. If the scores 346 are greater than the threshold, or satisfy the threshold, the sound may be associated with a cough. For example, if the scores 346 are less than the threshold, or do not satisfy the threshold, the sound may not be associated with a cough.

At 420, the process 400 may include determining, based at least in part on the score, whether a contagion has been introduced into the vehicle. For example, with the scores 346, the monitoring component 332 may be configured to determine whether the sound (e.g., cough) is indicative of contagion(s) being released into the vehicle 302. In some instances, whether contagion(s) have been introduced may be based on the determined symptom(s) of occupant, an occurrence of the symptom(s), a classifier of the symptom, and so forth.

At 422, the process 400 may include determining one or more action(s) to perform associated with preventing a spread of the contagion(s). That is, in instances where contagion(s) are introduced, action(s) may be performed to prevent the spread of the contagion amongst occupants in the vehicle 302. In some instances, the action(s) performed may be based on a severity or threat of the contagion(s) being introduced into the vehicle 302. As such, respective action(s) performed are responsive to a severity at which contagion(s) are introduced into the vehicle (e.g., sanitizing the vehicle 302 as compared to lowering windows of the vehicle 302).

In some instances, the run portion 404 may be configured to determine a health of the occupant and/or whether contagion(s) were introduced based at least in part on other data. For example, data collected by other sensors (e.g., perception data from one or more cameras in a passenger compartment, temperature data, etc.) may be input into the machine-learned model (or another machine-learned model) for use in determining the health of the occupant and/or whether contagion(s) were introduced.

FIG. 5 illustrates an example process 500 for classifying sounds captured within a vehicle for use in determining whether to sanitize the vehicle 302.

At 502 the process 500 may include receiving audio data associated with a sound captured in a vehicle. For example, microphone(s) within the vehicle may capture various sounds, such as user speech, coughs, road noise, motor noise, music, and so forth. In some instances, the audio data may be received according to predetermined schedules (e.g., every millisecond, every second, etc.), the audio data may be continuously received, and/or the audio data may be received responsive to detecting the sounds within the vehicle. In some instances, the audio data may be raw audio data and/or may be processed audio data (e.g., filtered) to remove background noise.

At 504 the process 500 may include determining that the sound was generated by an occupant of the vehicle. In some instances, determining whether the sound was generated by an occupant, as opposed to components of the vehicle (e.g., radio, road noise from tire, etc.) may include comparing an audio signature of the audio data against one or more reference audio signatures. For example, the audio data may include certain acoustic properties, and these acoustic properties may be compared against acoustic properties of the reference audio signatures to indicate whether the sound is indicative of a sound produced by the occupant. In some instances, this may involve a comparison of amplitudes, pitch, frequency, and so forth.

At 506 the process 500 may include associating the sound with the occupant. For example, the sound may be associated with a particular occupant in the vehicle. In instances where the vehicle includes multiple occupants, associating the sound with a particular occupant may allow for the tracking of sounds to determine, for example, a number of times the occupant coughed, sneezed, and so forth. In some instances, determining which occupant produced the sound may be based on energy levels within audio signals captured across an array of microphones, time of flight techniques, and so forth. In some instances, associating the sound with the occupant may also be determined using sensor data captured by other sensors in the vehicle (e.g., weight sensors indicating which seat(s) of the vehicle are being occupied, cameras in the vehicle indicating a location of occupants, and so forth).

At 508 the process 500 may include classifying the sound. For example, the sound may be classified as user speech, a cough, a sneeze, a sniffle, a throat clearing, and the like. In some instances, classifying the sound may involve inputting the audio data into machine-learned model(s) and receiving, as an output, an indication of the classifier. For example, the machine-learned model(s) may output scores that indicate a probability that the sound corresponds to user speech, a cough, and so forth. As discussed above, the machine-learned models may be previously trained to classify the sounds. Classifying the sound may also be based at least in part on extracting feature(s) associated with the sound, such as sound pressure levels, frequency, duration, and so forth.

Classifying the sounds may be used when determining whether the vehicle needs to be sanitized (e.g., to protect against the spread of germs). For example, if the sound corresponds to user speech, such sound may not be indicative of a health of the occupant and/or may not be indicative of contagion(s) being introduced into the vehicle. Comparatively, if the sound corresponds to a cough, such sound may be indicative of the occupant being sick and the release of contagion(s) within the vehicle. As such, by classifying the sound, it may be determined whether the sound is useful in diagnosing a health of the occupant and/or whether the vehicle is sanitized to protect against the spread of germs. In some instances, the process 500 may select a classifier with the highest probability. For example, if the machine-learned model(s) output a first score that the sound is associated with a cough, and a second score that the sound is associated with user speech, where the second score is less than the first score, the process 500 may determine that the sound corresponds to a cough.

In some instances, an audio signature associated with the sound may be compared against reference audio signatures to classify the sound. For example, the audio signatures may be compared to identify similarities or differences therebetween. If similar, or more than a threshold similarity, the sound may be classified as a cough, user speech, etc. In some instances, to compare the audio signatures, the audio data may be process by applying a fast Fourier transform to convert the audio signal into frequency domains. This may allow the audio signal to be analyzed under frequency domains.

At 510 the process 500 may include determining whether the classifier satisfies a first threshold. For example, as noted above, certain sounds may not be helpful in determining occupant health (e.g., user speech). As such, if the sound is user speech, such as the occupant requesting an increase in temperature within the vehicle, the classifier (user speech) may not satisfy the threshold. Comparatively, if the sound is classified as a cough or sneeze, for example, the classifier may satisfy the threshold because the sound may be helpful in determining occupant health (e.g., sick). More generally, however, the sound may be classified to indicate whether contagion(s) were introduced into the vehicle. If the process 500 determines that the classifier does not satisfy the threshold, the process 500 may follow the "NO" route and proceed to 512.

At 512 the process 500 may include determining to refrain from sanitizing the vehicle. For example, if the sound is associated with a sound that is not indicative of occupant health, or that contagion(s) were introduced, the process 500 may determine that the vehicle is sanitized (or does not need to be sanitized). For example, the sound captured may be commands, singing, speech between occupants of the vehicle, and so forth. In some instances, determining that the vehicle is does not need to be sanitized may include a determination that the vehicle is sanitized and does not need to be disinfected, and so forth. In some instances, a determination that the vehicle does not need to be sanitized may additionally, or alternatively, include a determination that the occupant is healthy. For example, if the occupant does not cough, sneeze, sniffle, and the like, or the occupant has allergies, for example, the occupant may not be releasing contagion(s) into the vehicle. From 512, the process 500 may proceed to 502 and receive additional audio data for use in determining whether the vehicle needs to be sanitized.

Alternatively, if at 510 the process 500 determines that the classifier satisfies the threshold, the process 500 may follow the "YES" route and proceed to 514. For example, the process 500 may determine that the sound is associated with a cough. At 514 the process 500 may include determining characteristic(s) associated with the sound. In some instances, determining characteristic(s) of the sound may include determining a frequency of the sound (e.g., time in between coughs), a duration of the sound (e.g., length of cough), a number of occurrences of the sound (e.g., number of coughs), a strength of the sound (e.g., a strength of the cough, such as sound pressure level, decibel level, etc.). In some instances, for some of these characteristic(s), such as the number of coughs, the process 500 may determine the number of coughs within the audio data and/or may determine the number of coughs across a plurality of audio data. In the latter instance, the process 500 may determine the number of coughs by accessing previously determined coughs associated with the occupant. This may be accomplished, at least in part, by associating the sound with the occupant, at 506. As such, the process 500 may be configured to access a profile associated with the occupant for use in determining the characteristic(s) associated with the sound.

At 516 the process 500 may include determining whether the characteristic(s) satisfy a second threshold. For example, the second threshold may be associated with a number coughs, a frequency of coughs over a certain period of time, a strength of the coughs, and/or a duration of the coughs. If the occupant coughs the threshold number of times, the characteristic(s) may be determined to satisfy the threshold. Additionally, or alternatively, if the occupant coughs longer than the threshold duration, the characteristic(s) may be determined to satisfy the threshold. Alternatively, if the occupant only coughs once over a certain period of time, the characteristic(s) may be determined to not satisfy the threshold. In some instances, any number of the characteristic(s) may be compared against respective thresholds for use in determining whether the characteristic(s) satisfy the second threshold. For example, if the occupant coughs ten times within a minute and satisfies the number of coughs thresholds, but the strength of the coughs does not satisfy the strength threshold, the characteristic(s) may satisfy the second threshold. In such instances, any number of the characteristic(s) may be compared against thresholds for use in determining the occupant health.

If at 516 the process 500 determines that the characteristic(s) do not satisfy the second threshold, the process 500 may follow the "NO" route and proceed to 512. In such instances, the process 500 may determine that the vehicle does not need to be sanitized. Such determination may also be indication of a lack of contagion(s) being introduced into the vehicle. For example, even though the occupant coughed, contagion(s) may not have been introduced into the vehicle (e.g., the occupant is not symptomatic). However, in some instances, based on detecting a cough, one or more preventative action(s) may be undertaken, such as lowering windows, purging cabin air, and so forth. Alternatively, if at 516 the process 500 determines that the characteristic(s) satisfy the second threshold, the process 500 may follow the "YES" route and proceed to 518.

At 518 the process 500 may include determining action(s) associated with disinfecting the vehicle and/or increasing a sanitization of the vehicle. For example, in instances where the characteristic(s) satisfy the second threshold, the process 500 may determine action(s), that when performed, serve to disinfect the vehicle. This may include action(s) that attempt to prevent the spread of contagion(s) within the vehicle and/or between occupant(s) in the vehicle. In some instances, the action(s) may include distributing cleansing agent(s) within the vehicle (e.g., liquid, vapor, gas, or combination thereof), scheduling the vehicle for maintenance (e.g., replace air filter), scheduling the service for cleaning, refraining from allowing additional occupant(s) to ride in the vehicle, lowering windows, deploying barrier(s) within the vehicle, providing warnings, increasing a ventilation/air circulation within the vehicle (e.g., circulating outside air within the vehicle), circulating the air through a HEPA filter, activating UV lights, and so forth. In some instances, the action(s) may limit contact or an air supply exchanged between occupants. In some instances, the action(s) may be determined, at least in part, on the classifier and/or the characteristic(s). For example, if the occupant is coughing severely, the action(s) may include refraining from picking up other occupants to ride in the vehicle within the occupant. Comparatively, if the occupant is coughing minimally, the action(s) may include refraining from picking up occupants for a period of time while the vehicle is being cleansed. The action(s) may also be based at least in part on a severity at which contagion(s) are introduced into the vehicle.

At 520 the process 500 may include causing the action(s) to be performed. For example, the vehicle may be sanitized, cleansed, or scheduled for service. In some instances, the action(s) may be performed while occupant(s) are in the vehicle and/or after the occupant(s) exit the vehicle. In some instances, first action(s) may be performed while the occupant(s) are in the vehicle (e.g., lowering windows) and second action(s) may be performed after the occupants exit the vehicle (e.g., sanitizing). After the action(s) are performed, the vehicle may be resumed for service. From 520, the process 500 may proceed to 502 whereby additional audio data may be received.

Although the process 500 is described as using audio data, other sensor data may be used. For example, the vehicle may include cameras that capture image data depicting the occupant (or an interior of the vehicle). The image data may be analyzed to determine physical characteristics of the occupant, such as perspiration, complexion, head in lap eye gaze, pupil dilation of the passenger, and so forth. Additional sensor data may include a temperature of the passenger compartment, a humidity of the passenger compartment, and so forth. Such characteristics may be utilized to determine the occupant health, a sanitization of the vehicle, and/or a release of contagions for use in determine action(s) to perform.

Example Clauses

The following paragraphs describe various examples. Any of the examples in this section may be used with any other of the examples in this section and/or any of the other examples or embodiments described herein.

A: A vehicle system comprising: a microphone; one or more processors; and one or more non-transitory computer-readable media storing instructions that, when executed by the one or more processors, cause the one or more processors to perform operations comprising: receiving, from the microphone, audio data corresponding to a sound captured in a vehicle; determining at least one characteristic associated with the sound; comparing the at least one characteristic to a threshold; determining, based at least in part on comparing the at least one characteristic to the threshold, that the sound is indicative of a contagion being introduced into the vehicle; and performing a mitigating action at the vehicle to limit a spread of the contagion.

B: The vehicle system of paragraph A, wherein the at least one characteristic comprises at least one of: a duration of the sound; a frequency at which the sound is detected; a sound pressure level associated with the sound; or a number of times the sound was detected.

C: The vehicle system of paragraph A or B, wherein the vehicle include a first occupant and a second occupant, the operations further comprising: determining a location of the sound within the vehicle; and associating, based at least in part on the location of the sound, the sound with the first occupant.

D: The vehicle system of any of paragraphs A-C, wherein the mitigating action comprises at least one of: scheduling the vehicle for cleaning; dispersing a cleansing agent within the vehicle; exposing an interior of the vehicle to ultraviolet light; actuating a window of the vehicle; controlling a heating ventilation and air conditioning (HVAC) system of the vehicle; causing the vehicle to come to a stop to permit one or more occupants of the vehicle to exit; or refraining from scheduling additional occupants to the vehicle.

E: A method comprising: receiving audio data generated by a microphone of a vehicle; associating the audio data with a sound produced by an occupant of the vehicle; determining a characteristic of the audio data; determining, based at least in part on the characteristic, that the audio data is indicative of a contagion being introduced within the vehicle; and performing a mitigating action to limit a spread of the contagion within the vehicle based at least in part on the determining that the audio data is indicative of the contagion being introduced within the vehicle.

F: The method of paragraph E, further comprising comparing the characteristic to a threshold, and wherein determining that the audio data is indicative of the contagion being introduced into the vehicle is further based at least in part on comparing the characteristic to the threshold.

G: The method of paragraph E or F, further comprising: inputting the sound into a machine learned model trained to classify sounds based on audio data; and receiving from the machine learned model a classification of the sound.

H: The method of any of paragraphs E-G, wherein the classification is associated with a cough, a sneeze, a sniffle, a virus, or other symptom in in which contagions are released.

I: The method of any of paragraphs E-H, further comprising: providing the audio data as an input to a machine-learned model; and generating, as an output from the machine-learned model, a score representing a likelihood of the contagion being introduced into the vehicle.

J: The method of any of paragraphs E-I, wherein the characteristic comprises at least one of: a frequency at which the occupant produces the sound; a duration of the sound; a number of times the occupant produces the sound; or a sound pressure level associated with the sound.

K: The method of any of paragraphs E-J, wherein the mitigating action comprises at least one of: scheduling the vehicle for cleaning; dispersing a cleansing agent within the vehicle; exposing an interior of the vehicle to ultraviolet light; actuating a window of the vehicle; controlling a heating ventilation and air conditioning (HVAC) system of the vehicle; prompting additional occupants to exit the vehicle; or refraining from scheduling additional occupants to the vehicle.

L: The method of any of paragraphs E-K, further comprising providing a notification to the occupant of the vehicle that is associated with the characteristic.

M: The method of any of paragraphs E-L, further comprising determining that the sound was generated by the occupant, and wherein associating the audio data with the occupant is based at least in part on determining that the sound was generated by the occupant.

N: The method of any of paragraphs E-M, further comprising determining a profile associated with the occupant, and wherein determining that the contagion was introduced into the vehicle is based at least in part on the profile.

O: The method of any of paragraphs E-N, further comprising: receiving sensor data captured by a sensor of the vehicle, the sensor data representing data other than audio data; and associating the sensor data with the occupant, and wherein determining that the contagion was introduced into the vehicle is further based at least in part on the sensor data.

P: One or more non-transitory computer readable media storing instructions executable by a processor, wherein the instructions, when executed, cause the processor to perform acts comprising: receiving audio data generated by a microphone of a vehicle; associating the audio data with a sound produced by an occupant of the vehicle; determining a characteristic of the audio data; determining, based at least in part on the characteristic, that the audio data is indicative of a contagion being introduced within the vehicle; and performing a mitigating action to limit a spread of the contagion within the vehicle based at least in part on the determining that the audio data is indicative of the contagion being introduced within the vehicle.

Q: The one or more non-transitory computer readable media of paragraph P, wherein the mitigating action comprises at least one of: scheduling the vehicle for cleaning; dispersing a cleansing agent within the vehicle; exposing an interior of the vehicle to ultraviolet light; actuating a window of the vehicle; controlling a heating ventilation and air conditioning (HVAC) system of the vehicle; prompting additional occupants to exit the vehicle; or refraining from scheduling additional occupants to the vehicle.

R: The one or more non-transitory computer readable media of paragraph P or Q, the acts further comprising further comprising comparing the characteristic to a threshold, and wherein determining that the audio data is indicative of the contagion being introduced into the vehicle is further based at least in part on comparing the characteristic to the threshold.

S: The one or more non-transitory computer readable media of any of paragraphs P-R, wherein the characteristic comprises at least one of: a frequency at which the occupant produces the sound; a duration of the sound; a number of times the occupant produces the sound; or a sound pressure level associated with the sound.

T: The one or more non-transitory computer readable media of any of paragraphs P-S, further comprising: inputting the sound into a machine learned model trained to classify sounds based on audio data; and receiving from the machine learned model a classification of the sound.

While the example clauses described above are described with respect to one particular implementation, it should be understood that, in the context of this document, the content of the example clauses can also be implemented via a method, device, system, computer-readable medium, and/or another implementation. Additionally, any of examples A-T can be implemented alone or in combination with any other one or more of the examples A-T.

CONCLUSION

While one or more examples of the techniques described herein have been described, various alterations, additions, permutations and equivalents thereof are included within the scope of the techniques described herein.

In the description of examples, reference is made to the accompanying drawings that form a part hereof, which show by way of illustration specific examples of the claimed subject matter. It is to be understood that other examples can be used and that changes or alterations, such as structural changes, can be made. Such examples, changes or alterations are not necessarily departures from the scope with respect to the intended claimed subject matter. While the steps herein can be presented in a certain order, in some cases the ordering can be changed so that certain inputs are provided at different times or in a different order without changing the function of the systems and methods described. The disclosed procedures could also be executed in different orders. Additionally, various computations that are herein need not be performed in the order disclosed, and other examples using alternative orderings of the computations could be readily implemented. In addition to being reordered, the computations could also be decomposed into sub-computations with the same results.

The invention claimed is:

1. A vehicle system comprising:

a microphone;

one or more processors; and one or more non-transitory computer-readable media storing instructions that, when executed by the one or more processors, cause the one or more processors to perform operations comprising:

receiving, from the microphone, first audio data corresponding to a first sound captured in a vehicle;

determining that the first sound was produced by an occupant of the vehicle;

providing, as an input to a machine-learned (ML) model, the first audio data;

receiving, as an output from the ML model, at least one first characteristic associated with the first sound;

receiving, from the microphone, second audio data corresponding to a second sound captured in the vehicle;

determining that the second sound was produced by the occupant of the vehicle;

determining at least one second characteristic associated with the second sound;

determining an identifier associated with the occupant;

determining, based at least in part on the identifier, a profile of the occupant;

determining, based at least in part on the profile, a first threshold associated with contagions being introduced into the vehicle;

comparing the at least one first characteristic to the first threshold;

comparing the at least one second characteristic to a second threshold;

determining, based at least in part on comparing the at least one first characteristic to the first threshold and comparing the at least one second characteristic to the second threshold, that the first sound and the second sound are indicative of a contagion being introduced into the vehicle;

storing, in association with the profile, an indication of the occupant introducing the contagion into the vehicle;

causing the vehicle to autonomously perform a mitigating action to limit a spread of the contagion, the mitigating action being controlling a heating and air conditioning (HVAC) system of the vehicle; and determining, based at least in part performing the mitigating action, that the vehicle is available to accept ride-share requests.

2. The vehicle system of claim 1, wherein:

the at least one first characteristic comprises at least one of:

a duration of the first sound, a frequency at which the first sound is detected, a sound pressure level associated with the first sound, or a number of times the first sound was detected; and the at least one second characteristic comprises at least one of:

a duration of the second sound, a frequency at which the second sound is detected, a sound pressure level associated with the second sound, or a number of times the second sound was detected.

3. The vehicle system of claim 1, wherein the mitigating action further comprises at least one of:

dispersing a cleansing agent within the vehicle;

actuating a window of the vehicle;

causing the vehicle to come to a stop to permit one or more occupants of the vehicle to exit; or determining that the vehicle is unavailable to be scheduled for additional occupants.

4. The vehicle system of claim 1, the operations further comprising determining, based at least in part on the profile, the second threshold, wherein the second threshold is associated with the contagions being introduced into the vehicle.

5. The vehicle system of claim 1, the operations further comprising:

receiving an indication associated with the occupant scheduling the vehicle;

determining the profile associated with the occupant; and determining, based at least in part on the profile, that the vehicle is limited to being scheduled for the occupant.

6. A method comprising:

receiving first audio data generated by a microphone of a vehicle;

associating the first audio data with a first sound produced by an occupant of the vehicle;

determining a first characteristic of the first audio data;

determining an identifier associated with the occupant;

determining, based at least in part on the identifier, a threshold associated with contagions being introduced into the vehicle;

comparing the first characteristic to the threshold;

determining, based at least in part on comparing the first characteristic to the threshold, that the first audio data is indicative of a contagion being introduced within the vehicle;

determining a first action to limit a spread of the contagion within the vehicle based at least in part on determining that the first audio data is indicative of the contagion being introduced within the vehicle, the first action including controlling an airflow within the vehicle;

causing, at a first time, performance of the first action;

receiving second audio data generated by the microphone of the vehicle, the second audio data being different than the first audio data;

associating the second audio data with a second sound produced by the occupant of the vehicle;

determining a second characteristic of the second audio data;

determining, based at least in part on the second characteristic, a second action to limit the spread of the contagion within the vehicle, the second action being different than the first action;

causing, at a second time that is after the first time, performance of the second action; and storing an indication in association with a profile of the occupant, the indication being used to limit ride-share requests of the occupant.

7. The method of claim 6, further comprising:
inputting the first sound into a machine learned model trained to classify sounds based on audio data; and
receiving from the machine learned model a classification of the first sound.

8. The method of claim 6, further comprising:
providing the first audio data as an input to a machine-learned model; and
generating, as an output from the machine-learned model, a score representing a likelihood of the contagion being introduced into the vehicle.

9. The method of claim 6, wherein the first characteristic comprises at least one of:
a frequency at which the occupant produces the first sound;
a duration of the first sound;
a number of times the occupant produces the first sound; or
a sound pressure level associated with the first sound.

10. The method of claim 6, wherein the first action or the second action comprises at least one of:
scheduling the vehicle for cleaning;
dispersing a cleansing agent within the vehicle;
exposing an interior of the vehicle to ultraviolet light;
actuating a window of the vehicle;
controlling a heating ventilation and air conditioning (HVAC) system of the vehicle;
prompting additional occupants to exit the vehicle; or
determining that the vehicle is unavailable to be scheduled for additional occupants.

11. The method of claim 6, further comprising providing a notification to the occupant of the vehicle, the notification being associated with the first characteristic.

12. The method of claim 6, further comprising determining that the first sound was generated by the occupant, and wherein associating the first audio data with the occupant is based at least in part on determining that the first sound was generated by the occupant.

13. The method of claim 6, further comprising determining, based at least in part on the identifier, the profile associated with the occupant, and wherein the threshold is stored in association with the profile.

14. The method of claim 6, further comprising:
receiving sensor data captured by a sensor of the vehicle, the sensor data representing data other than audio data; and
associating the sensor data with the occupant, and
wherein determining that the contagion was introduced into the vehicle is further based at least in part on the sensor data.

15. The method of claim 6, further comprising:
determining that the first characteristic fails to satisfy the threshold; and
based at least in part on determining that the first characteristic fails to satisfy the threshold, at least one of:
causing performance of the first action, or
refraining from causing performance of the second action.

16. One or more non-transitory computer readable media storing instructions executable by a processor, wherein the instructions, when executed, cause the processor to perform acts comprising:

receiving audio data generated by a microphone of a vehicle;
associating the audio data with a sound produced by an occupant of the vehicle;
determining a characteristic of the audio data;
determining an identifier associated with the occupant;
determining, based at least in part on the identifier, a threshold associated with a contagion being introduced within the vehicle;
comparing the characteristic to the threshold;
determining, based at least in part on comparing the characteristic to the threshold, that the audio data is indicative of the contagion being introduced within the vehicle;
causing the vehicle to perform a first action to limit a spread of the contagion based at least in part on determining that the audio data is indicative of the contagion being introduced within the vehicle, wherein the first action comprises controlling a heating ventilation and air conditioning (HVAC) system of the vehicle;
based at least in part on the contagion being introduced into the vehicle, determining that the vehicle is at least one of:
unavailable for ride-share requests, or
unable to be scheduled for other occupants;
storing an indication in association with a profile of the occupant, the indication being used to limit ride-share requests associated with the occupant;
causing the vehicle to perform a second action associated with cleansing the vehicle of the contagion; and
based at least in part on performing the second action, determining that the vehicle is at least one of:
available for the ride-share requests, or
able to be scheduled for the other occupants.

17. The one or more non-transitory computer readable media of claim 16, wherein the first action or the second action further comprises at least one of:
scheduling the vehicle for cleaning;
dispersing a cleansing agent within the vehicle;
exposing an interior of the vehicle to ultraviolet light;
actuating a window of the vehicle; or
prompting additional occupants to exit the vehicle.

18. The one or more non-transitory computer readable media of claim 16, wherein the characteristic comprises at least one of:
a frequency at which the occupant produces the sound;
a duration of the sound;
a number of times the occupant produces the sound; or
a sound pressure level associated with the sound.

19. The one or more non-transitory computer readable media of claim 16, further comprising:
inputting the sound into a machine learned model trained to classify sounds based on audio data; and
receiving from the machine learned model a classification of the sound.

20. The one or more non-transitory computer readable media of claim 16, further comprising receiving sensor data generated by a sensor of the vehicle, and wherein determining the characteristic of the audio data is based at least in part on the sensor data.

21. The one or more non-transitory computer readable media of claim 16, the acts further comprising providing, based at least in part on determining the characteristic, a notification to the occupant of the vehicle.

* * * * *